US008961405B2

(12) United States Patent
Murata

(10) Patent No.: US 8,961,405 B2
(45) Date of Patent: Feb. 24, 2015

(54) ENDOSCOPE SYSTEM HAVING DETECTION DEVICE FOR DETECTING TYPE OF DETACHABLY CONNECTED MODULE AND METHOD FOR OPERATING ENDOSCOPE SYSTEM

(75) Inventor: Masanao Murata, Tokyo (JP)

(73) Assignee: Olympus Corporation, Tokyo (JP)

( * ) Notice: Subject to any disclaimer, the term of this patent is extended or adjusted under 35 U.S.C. 154(b) by 1084 days.

(21) Appl. No.: 12/728,892

(22) Filed: Mar. 22, 2010

(65) Prior Publication Data

US 2010/0179385 A1 Jul. 15, 2010

Related U.S. Application Data

(63) Continuation of application No. 11/542,924, filed on Oct. 4, 2006, now Pat. No. 7,713,192.

(30) Foreign Application Priority Data

Jul. 29, 2005 (JP) .................................. 2005-221759

(51) Int. Cl.
*A61B 1/045* (2006.01)
*A61B 1/06* (2006.01)
(Continued)

(52) U.S. Cl.
CPC .............. *A61B 1/00059* (2013.01); *A61B 1/053* (2013.01); *A61B 1/0684* (2013.01);
(Continued)

(58) Field of Classification Search
CPC .. A61B 1/00059; A61B 1/053; A61B 1/0002; A61B 1/00057; A61B 1/045
USPC .......... 600/103, 109, 110, 117, 118, 175, 179
See application file for complete search history.

(56) References Cited

U.S. PATENT DOCUMENTS 4,295,406 A * 10/1981 Smith .......................... 84/470 R
4,344,701 A * 8/1982 Klose et al. ..................... 355/51
(Continued)

FOREIGN PATENT DOCUMENTS

JP 02-020817 1/1990
JP 05-040231 2/1993
(Continued)

OTHER PUBLICATIONS

Official Action, mailed Mar. 8, 2011, from the Japan Patent Office in counterpart Japanese Patent Application No. 2005-221759, together with a partial English language translation.

*Primary Examiner* — John P Leubecker
(74) *Attorney, Agent, or Firm* — Scully, Scott, Murphy & Presser, PC

(57) ABSTRACT

An endoscope system includes, in order to automatically detect a type of optical adapter and to generate to display an excellent image according to an intended purpose by performing an image signal processing control corresponding to the type of the optical adapter, a signal processing circuit for performing various image signal processings on an image signal from an image-pickup element, a plurality of optical adapters each including an image-formation optical system, adapter discriminating section, and LED, the optical adapters being detachably and selectively provided to the distal end of the endoscope section, and an apparatus main body including an image processing section for performing predetermined signal processing on the image signal from the signal processing circuit, an adapter detection section for detecting the adapter discrimination section, and a controller for controlling the whole endoscope system. At least driving control of the LED and various signal processing controls on the image signal obtained by the image-pickup element are performed based on the detection result of the adapter discrimination section by the adapter detection section.

11 Claims, 15 Drawing Sheets

(51) Int. Cl.
    *A61B 1/05*     (2006.01)
    *A61B 1/00*     (2006.01)
    *G02B 23/24*     (2006.01)

(52) U.S. Cl.
    CPC .......... *A61B 1/0676* (2013.01); *A61B 1/00105* (2013.01); *G02B 23/2423* (2013.01); *G02B 23/2461* (2013.01); *G02B 23/2476* (2013.01)
    USPC ............ 600/179; 600/175; 600/109; 600/118

(56) References Cited

U.S. PATENT DOCUMENTS

| | | | |
|---|---|---|---|
| 4,453,811 A * | 6/1984 | Yamasaki | 396/238 |
| 4,856,495 A | 8/1989 | Tohjoh et al. | |
| 4,884,133 A * | 11/1989 | Kanno et al. | 348/68 |
| 5,549,546 A * | 8/1996 | Schneider et al. | 604/26 |
| 5,570,129 A * | 10/1996 | Hafele et al. | 348/223.1 |
| 5,627,583 A * | 5/1997 | Nakamura et al. | 348/72 |
| 5,865,749 A * | 2/1999 | Doten et al. | 600/443 |
| 5,910,816 A | 6/1999 | Fontenot et al. | |
| 6,002,425 A * | 12/1999 | Yamanaka et al. | 348/68 |
| 6,063,023 A * | 5/2000 | Sakiyama et al. | 600/118 |
| 6,092,722 A | 7/2000 | Heinrichs et al. | |
| 6,241,656 B1 * | 6/2001 | Suga | 600/109 |
| 6,485,414 B1 | 11/2002 | Neuberger | |
| 6,796,939 B1 | 9/2004 | Hirata et al. | |
| 7,170,046 B2 | 1/2007 | Higashitsutsumi | |
| 7,413,543 B2 | 8/2008 | Banik et al. | |
| 7,850,606 B2 * | 12/2010 | Yokota | 600/175 |
| 2002/0156349 A1 * | 10/2002 | Yamaki et al. | 600/178 |
| 2003/0142205 A1 * | 7/2003 | Takahashi et al. | 348/65 |
| 2003/0160865 A1 | 8/2003 | Takahashi | |
| 2003/0174205 A1 * | 9/2003 | Amling et al. | 348/65 |
| 2004/0143157 A1 * | 7/2004 | Doguchi et al. | 600/109 |
| 2005/0014996 A1 * | 1/2005 | Konomura et al. | 600/175 |
| 2005/0020879 A1 * | 1/2005 | Suzuki | 600/118 |
| 2005/0157168 A1 * | 7/2005 | Kaneko | 348/72 |
| 2005/0177027 A1 * | 8/2005 | Hirata | 600/179 |
| 2006/0020168 A1 | 1/2006 | Naruse | |
| 2006/0058584 A1 | 3/2006 | Hirata | |
| 2006/0069309 A1 | 3/2006 | Ono | |
| 2006/0183977 A1 | 8/2006 | Ishigami et al. | |
| 2006/0217594 A1 | 9/2006 | Ferguson | |
| 2007/0049802 A1 | 3/2007 | Yokota | |
| 2007/0100207 A1 * | 5/2007 | Ueno et al. | 600/160 |
| 2008/0021272 A1 * | 1/2008 | Doguchi et al. | 600/109 |

FOREIGN PATENT DOCUMENTS

| | | |
|---|---|---|
| JP | 05-049600 | 3/1993 |
| JP | 2001-061777 | 3/2001 |
| JP | 2004-033487 | 2/2004 |
| JP | 2006-158516 | 6/2006 |

\* cited by examiner

FIG.18

| | | TYPE OF OPTICAL ADAPTER | NUMBER OF LED | OPTICAL SYSTEM | | | | RELATIVE COMPARISON OF BRIGHTNESS LEVEL (DARK) ←→ (BRIGHT) |
|---|---|---|---|---|---|---|---|---|
| | | | | FIELD OF VIEW | DIRECTION OF VIEW | DEPTH OF OBSERVATION | F No. | |
| FOR OBSERVATION | LARGE-DIAMETER ENDOSCOPE | 40D | 16 | 40° | DIRECT VIEWING | 200~∞mm | 2.4 | ○ (bright) |
| | | 80D/NF | 14 | 80° | | 8~∞mm | 9.5 | ○ |
| | | (A) 80D/FF | 14 | 80° | | 35~∞mm | 3.1 | ○ |
| | | 120D/NF | 12 | 120° | | 4~190mm | 9.2 | |
| | | 120D/FF | 12 | 120° | | 25~∞mm | 3.3 | |
| | | 80S | 14 | 80° | SIDE VIEWING | 200~∞mm | 3.7 | ○ |
| | | (B) 120S/NF | 12 | 120° | | 8~∞mm | 9.6 | ○ |
| | | 120S/FF | 12 | 120° | | 35~∞mm | 6.0 | ○ |
| | SMALL-DIAMETER ENDOSCOPE | 40D | 6 | 40° | DIRECT VIEWING | 200~∞mm | 2.4 | ○ |
| | | 80D/NF | 8 | 80° | | 8~∞mm | 9.5 | ○ |
| | | 80D/FF | 8 | 80° | | 35~∞mm | 3.1 | ○ |
| | | 120D/NF | 2 | 120° | | 4~190mm | 9.2 | ○ |
| | | 120D/FF | 2 | 120° | | 25~∞mm | 3.3 | ○ |
| | | 80S | 8 | 80° | SIDE VIEWING | 18~∞mm | 4.0 | ○ |
| | | 120S/NF | 4 | 120° | | 1~∞mm | 9.6 | ○ |
| | | 120S/FF | 4 | 120° | | 5~∞mm | 5.9 | ○ |
| | | 100D/100S | 6 | 100°/100° | DIRECT VIEWING/SIDE VIEWING | 2~∞mm | 7.0 | ○ |
| | | 220D | 6 | 220° | DIRECT VIEWING | 2~∞mm | 4.3 | ○ |
| FOR MEASUREMENT | LARGE-DIAMETER ENDOSCOPE | (C) 60D/60D | 10 | 60° | DIRECT VIEWING | 5~∞mm | 7.5 | ○ |
| | | 50S/50S | 12 | 50° | SIDE VIEWING | 4~∞mm | | ○ |
| | SMALL-DIAMETER ENDOSCOPE | 60D/60D | 2 | 60° | DIRECT VIEWING | 5~∞mm | 7.5 | ○ |
| | | 60S/60S | 4 | 60° | SIDE VIEWING | 4~∞mm | | ○ |
| FOR SPECIAL PURPOSE | INFRARED | (D) 80D | 8 | 80° | DIRECT VIEWING | 35~∞mm | 3.1 | ○ |
| | FLUORESCENT (ULTRAVIOLET) | (E) 80D | 6 | 80° | DIRECT VIEWING | 35~∞mm | 3.1 | ○ |

FIG.19

CORRESPONDING EXAMPLE OF TYPE OF OPTICAL ADAPTER AND SIGNAL PROCESSING CORRECTION ITEM

| TYPE OF OPTICAL ADAPTER | | | | | CORRECTION ITEMS | | | | | | | | | |
|---|---|---|---|---|---|---|---|---|---|---|---|---|---|---|
| INTENDED PURPOSE | APPLICABLE ENDOSCOPE | | AGC MAXIMUM GAIN VALUE a (MAX) | AGC MINIMUM GAIN VALUE a (min) | BRIGHT SET VALUE b | ELECTRONIC SHUTTER CONTROL c | CCD DRIVE CONTROL d | γ CORRECTION CONTROL e | WIDE D RANGE CONTROL f | COLOR TONE CONTROL g | IMAGE PROCESSING CONTROL h | ENCODER CONTROL i | LED DRIVE CONTROL SIGNAL j |
| FOR DIRECT VIEWING/ FOR SIDE VIEWING | LARGE-DIAMETER | (A) 80D /FF | SET MAX (n) CURVE | SET min (n) CURVE | STANDARD SETTING (S) | ELECTRONIC SHUTTER VALID (FROM 1/60 TO 1/10000 SECONDS) | LONG-TIME EXPOSURE SETTING VALID (FROM 2 TO 1/60 SECONDS) | STANDARD | STANDARD SETTING | STANDARD SETTING | ONLY ENHANCEMENT PROCESSING VALID | STANDARD | SET DRIVE CURRENT FOR DRIVING FOURTEEN WHITE LEDS |
| FOR DIRECT VIEWING/ FOR SIDE VIEWING | SMALL-DIAMETER | (B) 120S /NF | SET MAX (1) CURVE | SET min (1) CURVE | STANDARD SETTING (S) | ELECTRONIC SHUTTER FUNCTION (FROM 1/120 TO 1/20000 SECONDS) | LONG-TIME EXPOSURE SETTING VALID (FROM 4 TO 1/60 SECONDS) | BLACK CORRECTION | BRIGHTNESS CORRECTION | STANDARD SETTING | ONLY FIELD STORAGE SENSITIZATION (UP TO 4 TIMES) VALID | STANDARD | SET DRIVE CURRENT FOR DRIVING TWELVE WHITE LEDS |
| FOR MEASUREMENT | | (C) 60D /60D | SET MAX (1) CURVE | SET min (n) CURVE | STANDARD (S) DARKER SETTING (L) | ELECTRONIC SHUTTER VALID (FROM 1/60 TO 1/20000 SECONDS) | LONG-TIME EXPOSURE SETTING INVALID | LINEAR CORRECTION | NO CORRECTION | STANDARD SETTING | ONLY MEASUREMENT PROCESSING VALID | STANDARD | SET DRIVE CURRENT FOR DRIVING TEN WHITE LEDS |
| | INFRARED | (D) 80D | SET MAX (SPH) CURVE | SET min (1) CURVE | STANDARD (S) BRIGHTER SETTING (H) | ELECTRONIC SHUTTER INVALID | LONG-TIME EXPOSURE SETTING VALID (FROM 10 TO 1/60 SECONDS) | BLACK CORRECTION | BRIGHTNESS CORRECTION | MONOCHROME SETTING | ONLY FIELD STORAGE SENSITIZATION (UP TO 16 TIMES) VALID | Y LEVEL (2 TIMES) C LEVEL (0.1 TIMES) | SET DRIVE CURRENT FOR DRIVING EIGHT INFRARED LEDS |
| FOR SPECIAL PURPOSE | FLUORESCENT (ULTRAVIOLET) | (E) 80D | SET MAX (2) CURVE | SET min (2) CURVE | STANDARD (S) BRIGHTER SETTING (H) | ELECTRONIC SHUTTER VALID | LONG-TIME EXPOSURE SETTING VALID (FROM 2 TO 1/60 SECONDS) | BRIGHTNESS CORRECTION | BRIGHTNESS CORRECTION | STANDARD SETTING | ONLY FIELD STORAGE SENSITIZATION (UP TO 4 TIMES) VALID | Y LEVEL (1.0 TIMES) C LEVEL (2.0 TIMES) | SET DRIVE CURRENT FOR DRIVING SIX ULTRAVIOLET LEDS |

ENDOSCOPE SYSTEM HAVING DETECTION DEVICE FOR DETECTING TYPE OF DETACHABLY CONNECTED MODULE AND METHOD FOR OPERATING ENDOSCOPE SYSTEM

RELATED APPLICATIONS

This application is a continuation of U.S. Ser. No. 11/542,924, filed Oct. 4, 2006, the entire contents of which is incorporated herein by reference.

BACKGROUND OF THE INVENTION

1. Field of the Invention

The present invention generally relates to an endoscope system, and more particularly, to an endoscope system including an optical adapter which is selected among a plurality of LED illumination built-in type optical adapters according to an intended purpose, and is detachably provided to a distal end of an insertion section of an endoscope.

2. Related Background Art

In recent years, there has been generally put to practical use an endoscope system capable of observing an organ and the like in a body cavity by inserting an elongated insertion section into the body cavity, and performing various therapeutic treatments by using a treatment instrument inserted in a treatment instrument inserting channel as needed.

In addition, in an industrial field, a similar industrial endoscope system is widely used in observing or inspecting (image measuring processing) a flaw, corrosion, etc., inside of a boiler, turbine, engine, chemical plant, or the like.

As such a conventional endoscope system, there is an endoscope system including an electronic endoscope which is configured to have a photoelectric conversion element for receiving an optical image and photoelectrically converting the image into an electric signal representing the image (referred to as an image signal), for example an image-pickup element such as CCD (Charge Coupled Device) and the like, provided to a distal end of an insertion section of the endoscope.

In the endoscope system including such an electronic endoscope (hereinafter referred to simply as an endoscope), after various signal processings are performed on an image signal generated based on an optical image (observation image) of an object of shooting formed on a photoelectric conversion surface of an image-pickup element, an endoscope image can be displayed and observed by outputting the image on a monitor device such as a liquid crystal display (LCD) and the like.

As for an industrial endoscope system in particular, there is an endoscope system configured such that an optical adapter is detachably provided to a distal end of an insertion section of an endoscope so as to perform an appropriate observation, image measuring processing, and the like, depending on a part to be inspected. In addition, there is put to practical use an endoscope system configured such that a desired observation and an inspection and the like including image measuring processing can be performed by selecting an optical adapter among a plurality of types of optical adapters according to a desired purpose and attaching the selected optical adapter to a distal end of an insertion section of an endoscope.

The types of optical adapters detachably provided to a distal end of an insertion section of an endoscope includes, for example, types for direct-viewing observation and side-viewing observation, for large-diameter tube and small-diameter tube, for proximal observation and distal observation, and the like, and in addition, those for stereoscopic observation and image measuring processing, which are provided with two observation optical systems (referred to as stereo optical system), those capable of infrared observation or fluorescent special observation as a special purpose, and the like.

Among these, as for the optical adapter for proximal observation, for example, an aperture value (FNo.; F-number) thereof is set larger so as to obtain deep field of depth. On the other hand, as for the optical adapter for distal observation, the aperture value thereof is set smaller so as to be able to perform an observation even with a small amount of illumination light. Furthermore, as for the optical adapter for measurement provided with the stereo optical system, it is usual that the aperture value is set larger. Thus, the optical adapter detachably provided to a distal end of an insertion section of an endoscope includes an aperture means of which aperture value is set according to an intended purpose.

In addition, the conventional endoscope system, in which a plurality of types of optical adapters are prepared and an optical adapter is arbitrarily selected and used according to a desired purpose, sometimes requires different controls depending on the types of the optical adapters attached to the distal end of the insertion section of the endoscope.

Therefore, there is proposed an endoscope system capable of detecting the type of an optical adapter which is attached to a distal end of an insertion section of an endoscope, in Japanese Patent Laying-open No. 2004-33487, for example.

The endoscope system disclosed by Japanese Patent Laying-open No. 2004-33487 described above includes an identification section, provided to an optical adapter detachably attached to a distal end of an insertion section of an endoscope, for identifying a type of the optical adapter, and further includes, in a control section of an endoscope main body, a discrimination section for detecting an identification section of the attached optical adapter and discriminating the type of the attached optical adapter, and notifying means for notifying a user of a discrimination result from the discrimination section, or an adapter information specification section which reads adapter information corresponding to the attached optical adapter from among adapter information items, which are registered in advance with respect to each type of optical adapter, based on the discrimination result sent from the discrimination section, and specifies the adapter information.

With such a configuration, in the endoscope system according to the publication, the control section of the endoscope main body detects the identification section of the optical adapter attached to the distal end of the insertion section of the endoscope by the discrimination section, discriminates the types of the attached optical adapters, and notifies the discrimination result to a user, or reads necessary adapter information based on the discrimination result and specifies the adapter information.

With such a configuration, the user can easily confirm that a desired optical adapter is attached to the distal end of the insertion section of the endoscope, and can prevent a mistake of attaching a wrong optical adapter.

Meanwhile, in recent years, there are various proposals on an LED illumination built-in type endoscope system, in which a light-emitting diode (LED) which has a small size and can be driven with low electric power is built in an optical adapter, instead of a conventionally utilized metal halide lamp and the like, as light source means for irradiating an object to be observed with illumination light.

SUMMARY OF THE INVENTION

An endoscope system according to the present invention is an endoscope system provided with an image-pickup element at a distal end of an insertion section, the system comprises: a signal processing circuit for performing various image signal processings on an image signal from the image-pickup element; a plurality of LED illumination built-in type optical adapters each including image-formation optical system means, adapter discrimination means, and LED illumination means, the plurality of optical adapters being detachably and selectively provided to a distal end of an endoscope section; and an apparatus main body including an image processing section for receiving an image signal from the signal processing circuit and performing predetermined signal processing on the image signal, an adapter detection section for detecting the adapter discrimination means of the optical adapters, and control means for controlling the whole endoscope system; in which at least driving control of the LED illumination means and various signal processing control on the image signal obtained by the image-pickup element are performed based on the detection result of the adapter discrimination means by the adapter detection section.

The advantages of the present invention will be more apparent from the following detailed description.

BRIEF DESCRIPTION OF THE DRAWINGS

FIG. 18 is a diagram showing in a tabular form specific examples of the types of optical adapters in the endoscope system in FIG. 1; and FIG. 19 is a diagram showing in a tabular form corresponding examples of the types of optical adapters and signal processing correction items in the endoscope system in FIG. 1.

DETAILED DESCRIPTION OF THE PREFERRED EMBODIMENTS

FIGS. 1 to 19 are diagrams describing an endoscope system according to an embodiment of the present invention.

Firstly, general description will be made on a configuration of an endoscope system 1 according to the present embodiment with reference to FIGS. 1 and 2 below.

Figure 1:
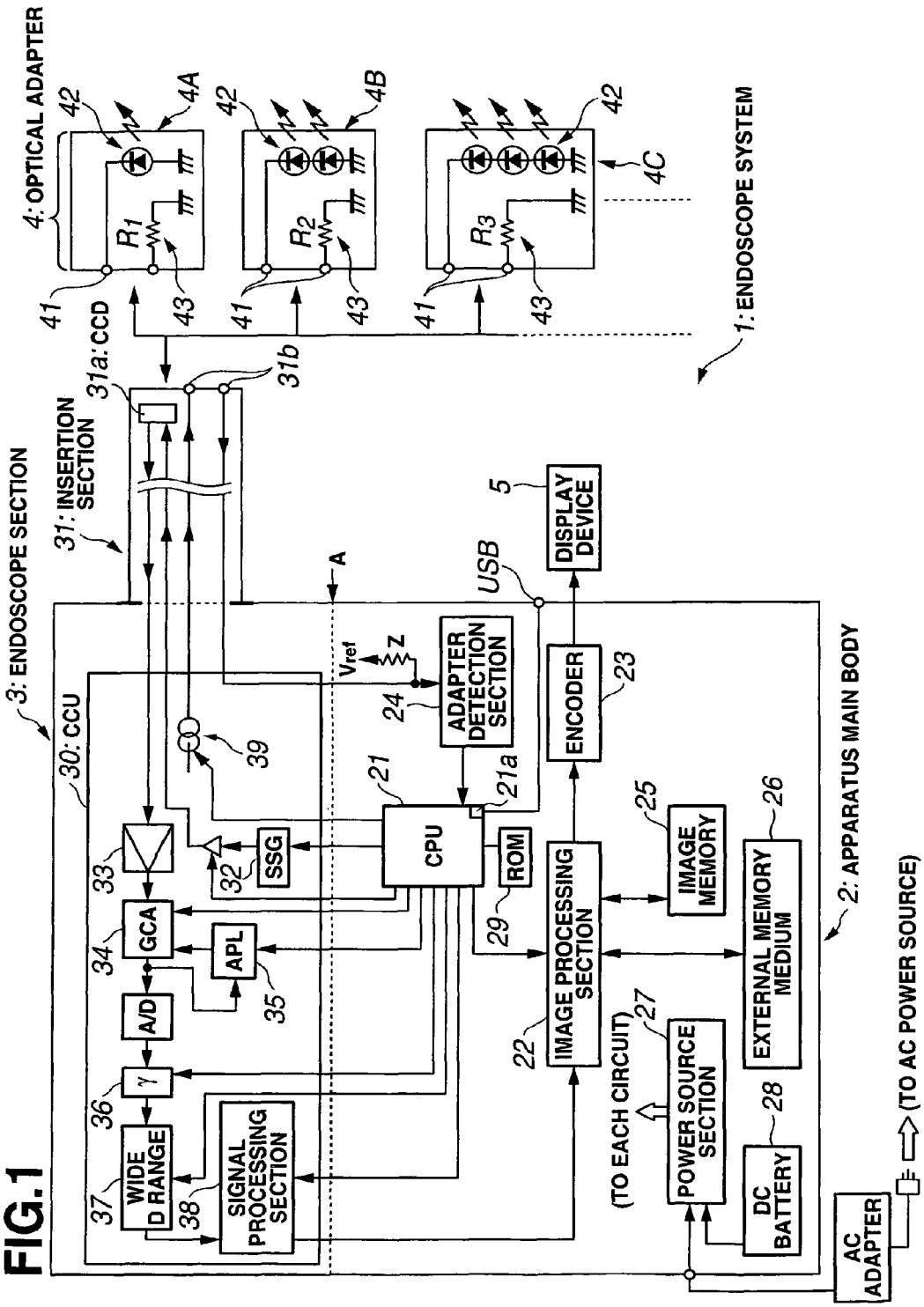
FIG. 1 is a block configuration diagram schematically showing mainly an electric circuit configuration of an endoscope system according to an embodiment of the present invention.
Figure 2:
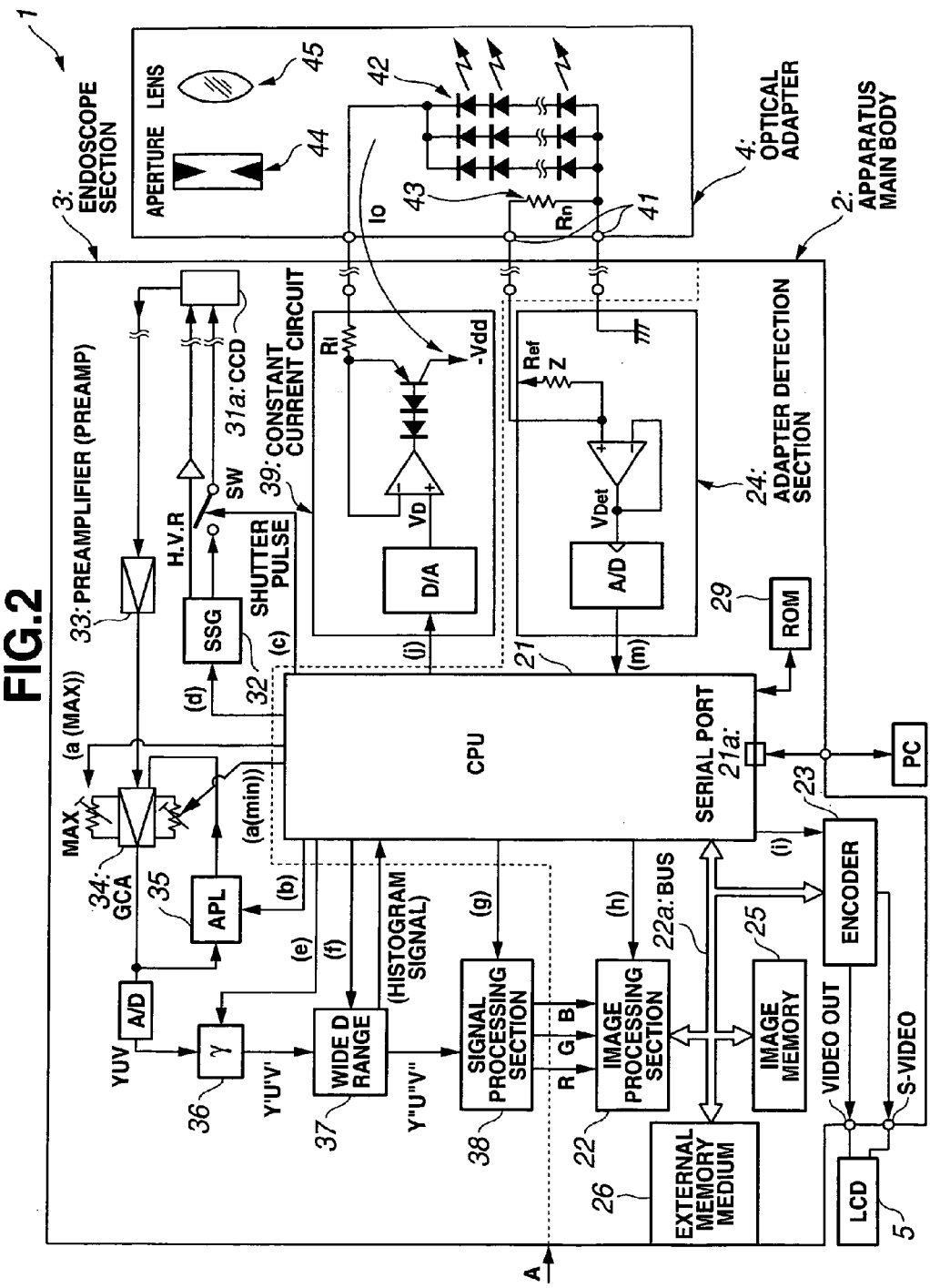
FIG. 2 is a block configuration diagram showing a circuit configuration and a signal transmission path of the endoscope system in FIG. 1.

As shown in FIGS. 1 and 2, the endoscope system 1 according to the present embodiment includes, for example, an apparatus main body 2 having inside thereof a control circuit including, for example, a CPU 21 which is control means for controlling the whole endoscope system 1 and respective signal processing circuits for performing various signal processings and the like, an endoscope section 3 formed with a camera control unit (CCU) 30, an insertion section 31, and the like, which is configured to be freely detachable from the apparatus main body 2, a plurality of LED illumination built-in type optical adapters (hereinafter, simply referred to as optical adapters) 4 which are configured to be freely detachable from the distal end of the insertion section 31 of the endoscope section 3, a display device 5, connected to the apparatus main body 2, for displaying an endoscope image and the like, an AC adapter 6 (diagrammatic representation is omitted in FIG. 2), connected to an AC power source and the like, for supplying driving power to the endoscope system 1.

The apparatus main body 2 and the endoscope section 3 are configured as individual units so as to separate from each other along a dotted line portion shown by arrows A in FIGS. 1 and 2. Accordingly, the scope section 3 is detachably provided to the apparatus main body 2.

Therefore, the endoscope system 1 is configured by properly selecting the desired endoscope section 3 corresponding to a desired purpose among a plurality of types of endoscope sections 3 which are different depending on intended purposes, and attaching the selected endoscope section 3 to the apparatus main body 2.

Note that the detachable mechanism of the apparatus main body 2 and the endoscope section 3 is not directly related to the summary of the present invention, so that detailed description thereof will be omitted.

The CPU 21 of the apparatus main body 2 is control means for controlling the whole endoscope system 1, as described above. Furthermore, as described later in detail, the CPU 21 discriminates the type of the optical adapter 4 attached to the distal end of the insertion section 31 of the endoscope section 3 by detecting adapter discrimination means (resistor 43) with an adapter detection section 24. Then, based on the discrimination result, the CPU 21 reads various setting control data corresponding to the type of the attached optical adapter 4 from storage means such as a ROM 29. Based on the various setting control data thus read, the CPU 21 controls the driving of LED illumination means (light-emitting diode 42) of the optical adapter 4 and various signal processing on an image signal obtained by an image-pickup element 31*a*, by transmitting predetermined setting control signals to the respective circuits.

In this case, the setting control signals transmitted from the CPU 21 to the respective circuits are shown by the numerals, a (MAX), a (min), b to h in FIG. 2.

Now, description will be made below on a definition of each item of the setting control signals a (MAX), a (min), and b to h.

Figure 5:
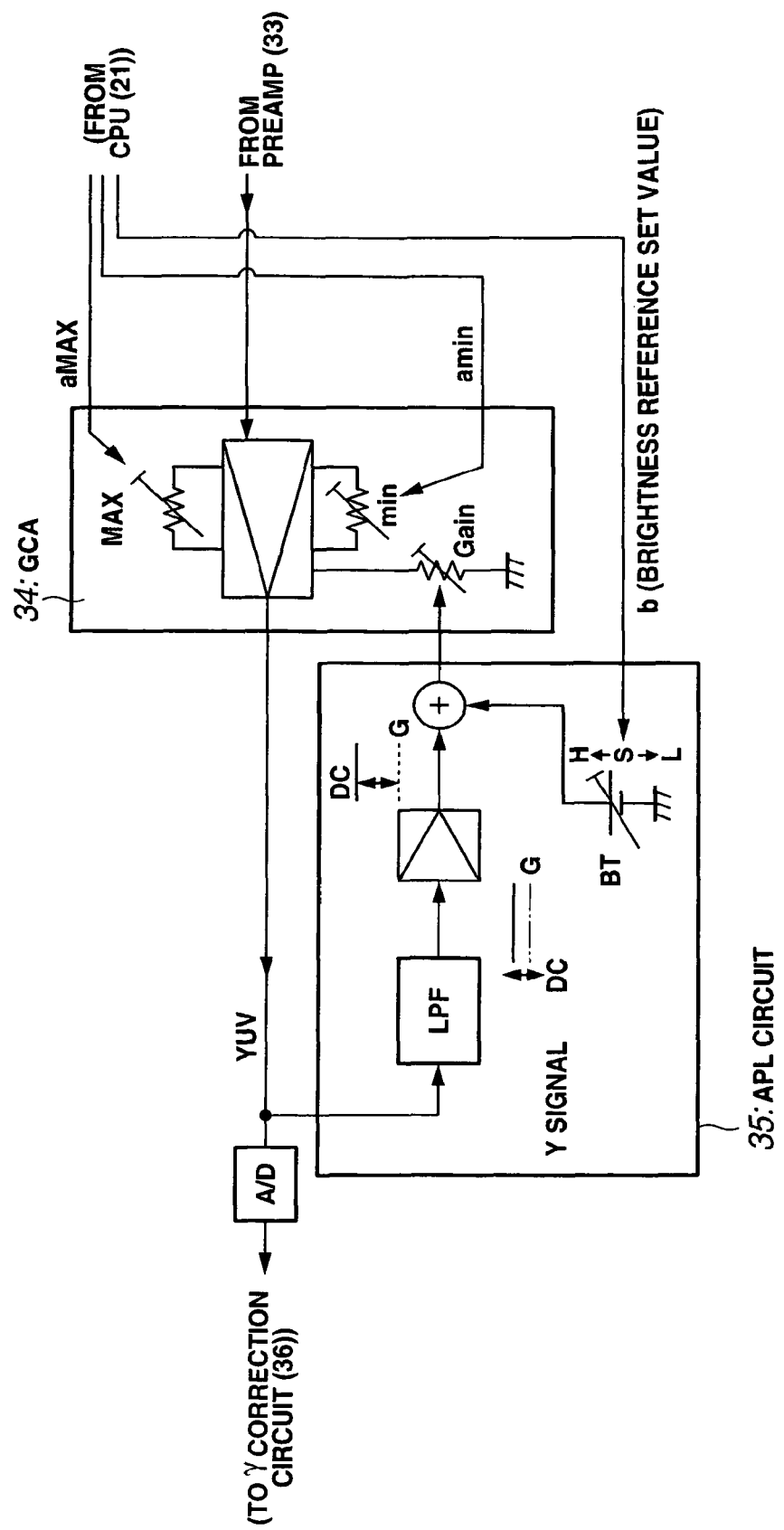
FIG. 5 is a diagram schematically showing internal circuit configurations of a GCA circuit and an APL circuit extracted from the components of the endoscope system in FIG. 1.

The setting control signal a (MAX) is a control signal for setting the maximum gain value of AGC (Automatic Gain Control) processing by a GCA circuit 34 (See FIGS. 2, 5).

The setting control signal a (min) is a control signal for setting the minimum gain value of AGC (Automatic Gain Control) processing by the GCA circuit 34 (See FIGS. 2, 5).

The setting control signal b is a control signal for setting a brightness reference set value for APL (Average Picture Level (Average of Picture Range) for setting brightness level of a screen) control by an APL circuit 35 (See FIGS. 2, 5).

The setting control signal c is a control signal for controlling an electronic shutter by a switch SW, that is, an electronic shutter control pulse (See FIG. 2).

The setting control signal d is a CCD drive control signal for controlling the driving of the image-pickup element 31*a* by a Synchronized Signal Generator (hereinafter, referred to as SSG) 32, as well as a control signal for setting a shutter speed for long-time exposure by intermittently operating the image-pickup element 31*a* (See FIG. 2).

Figure 8:
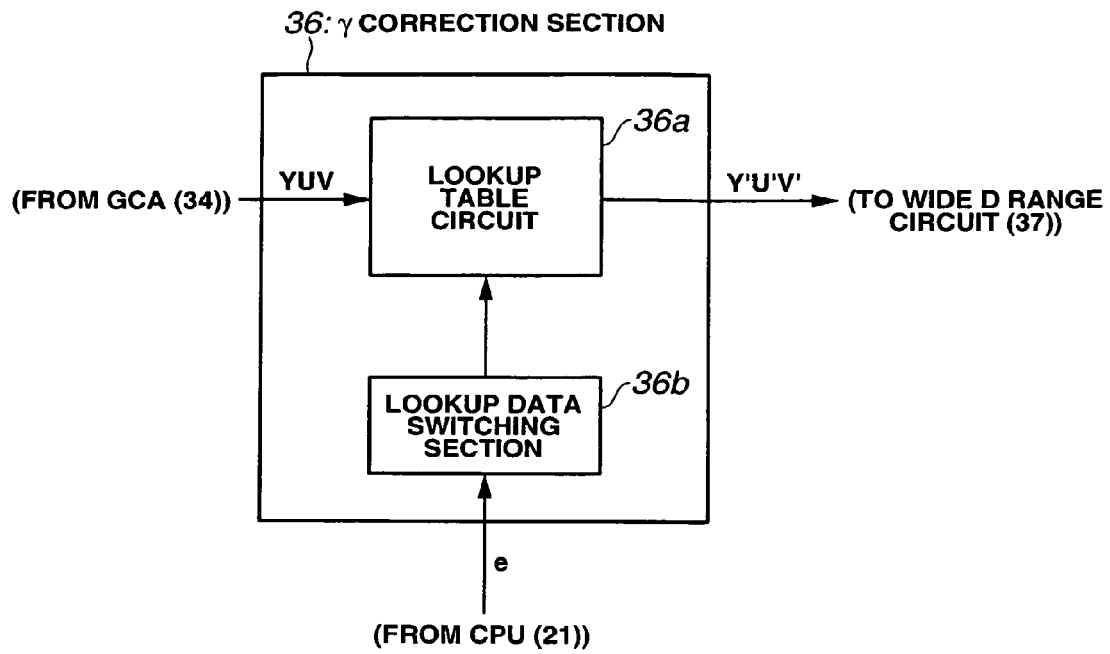
FIG. 8 is a diagram schematically showing an internal circuit configuration of a gamma (γ) correction section extracted from the components of the endoscope system in FIG. 1.

The setting control signal e is a control signal for setting a γ correction value by a γ correction section 36 (See FIGS. 2, 8).

Figure 10:
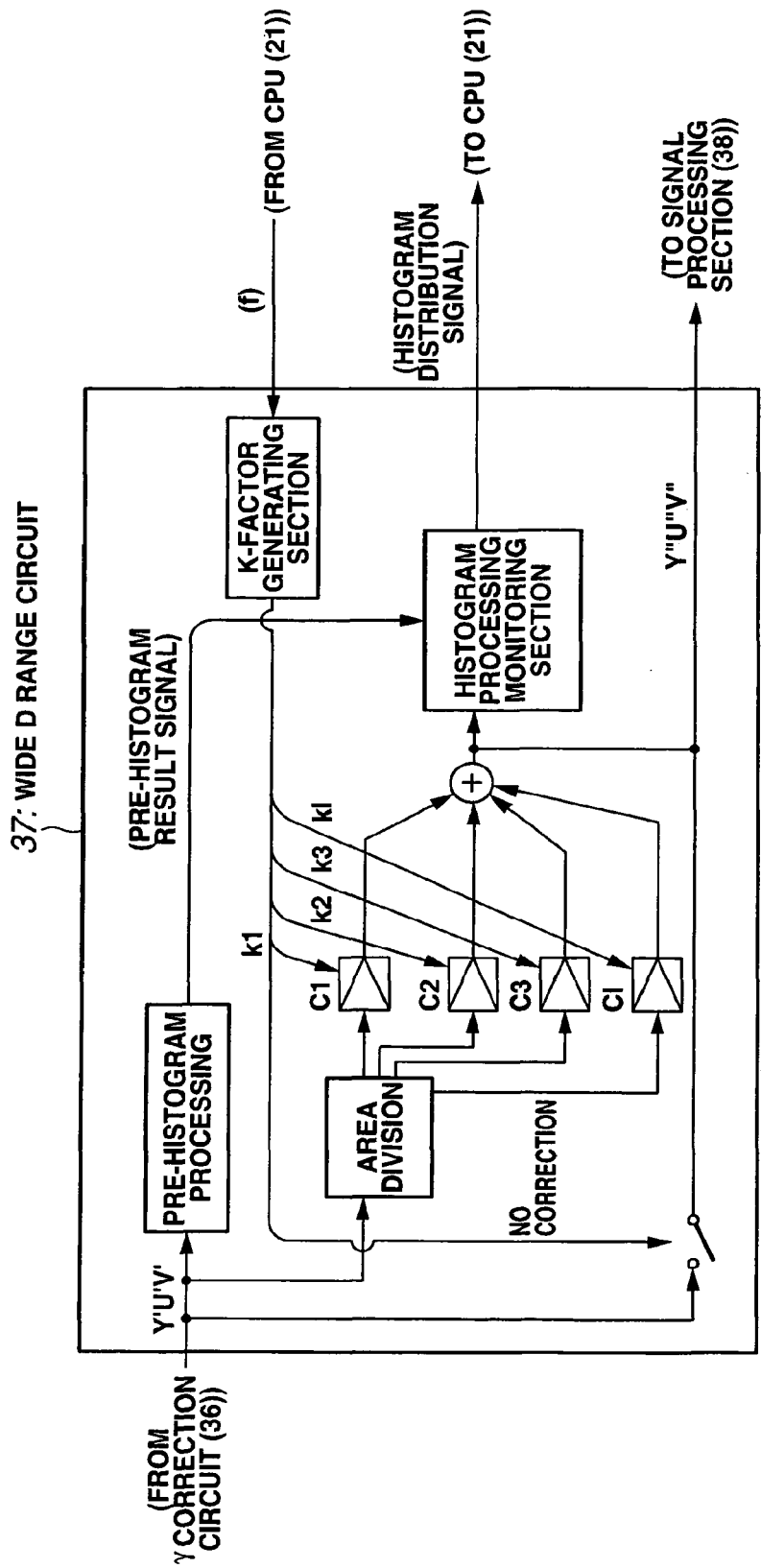
FIG. 10 is a diagram schematically showing an internal circuit configuration of a wide dynamic range circuit extracted from the components of the endoscope system in FIG. 1.
Figure 14:
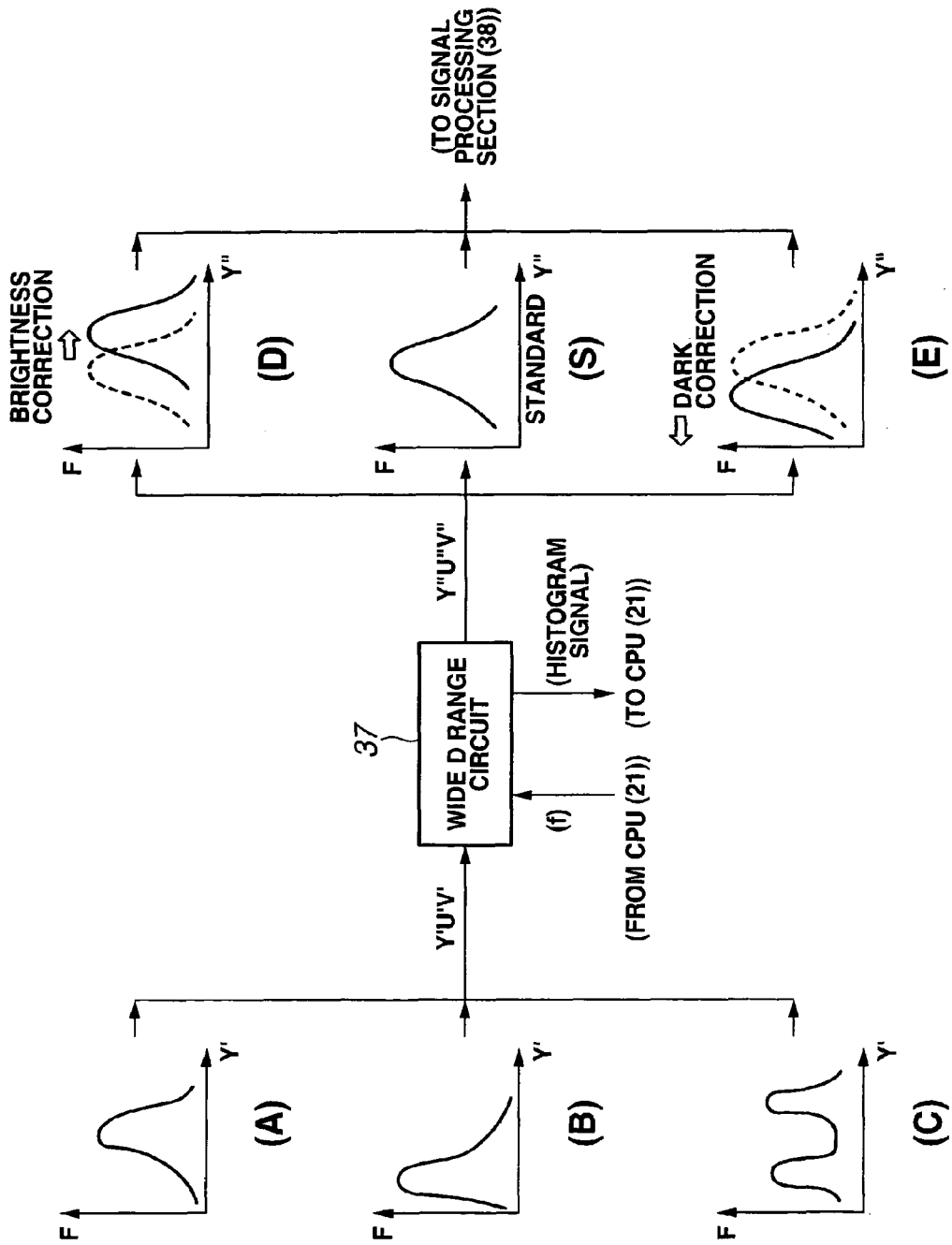
FIG. 14 is a diagram describing an operation of the wide dynamic range circuit in FIG. 10.

The setting control signal f is a control signal for setting brightness correction (black compression/white compression correction) of an image by a wide dynamic range circuit 37 (See FIGS. 2, 10, and 14).

Figure 15:
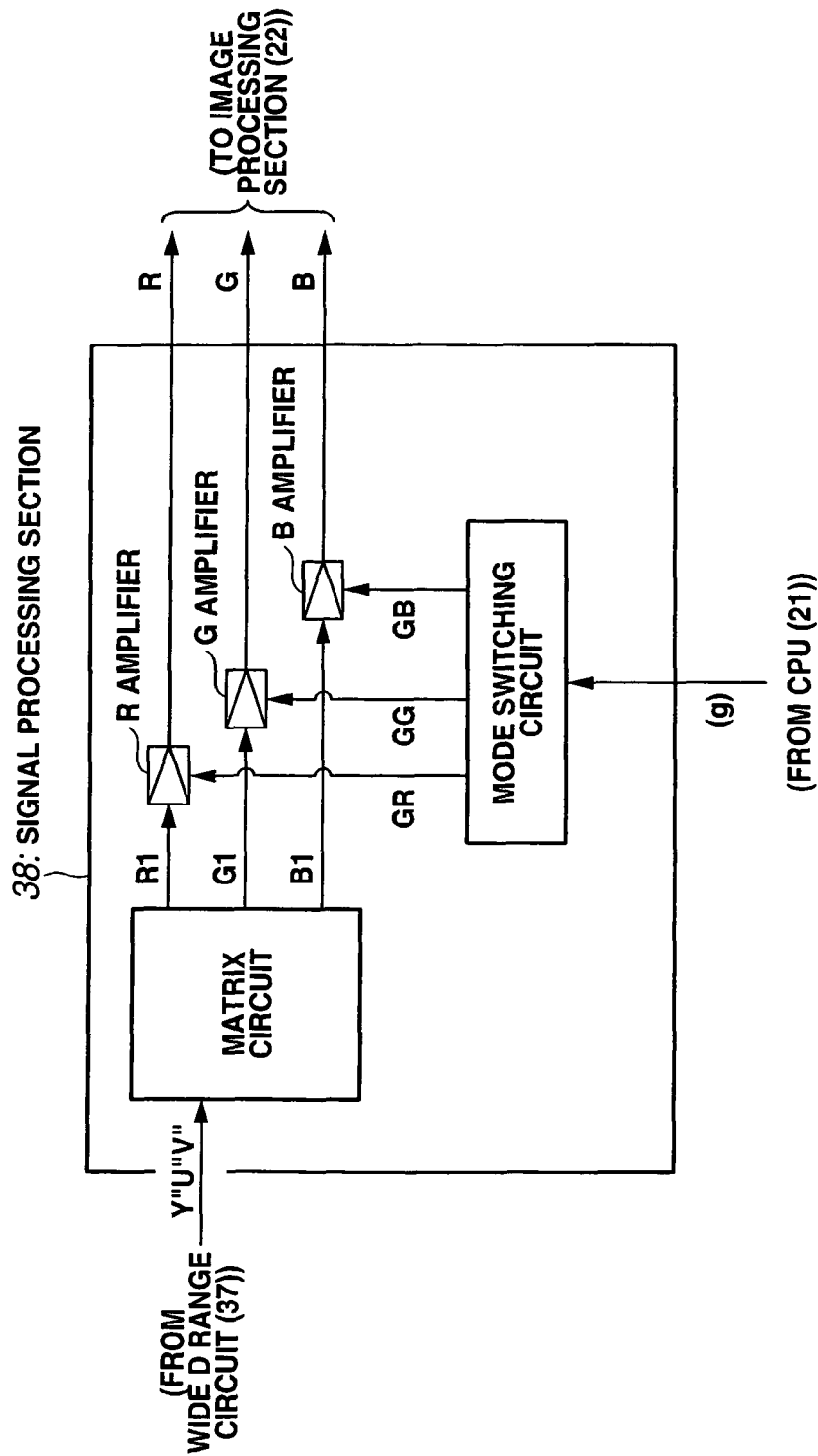
FIG. 15 is a diagram schematically showing an internal circuit configuration of a signal processing section extracted from the components of the endoscope system in FIG. 1.

The setting control signal g is a control signal for controlling a color tone of an image by a signal processing section 38 (See FIGS. 2, 15).

Figure 16:
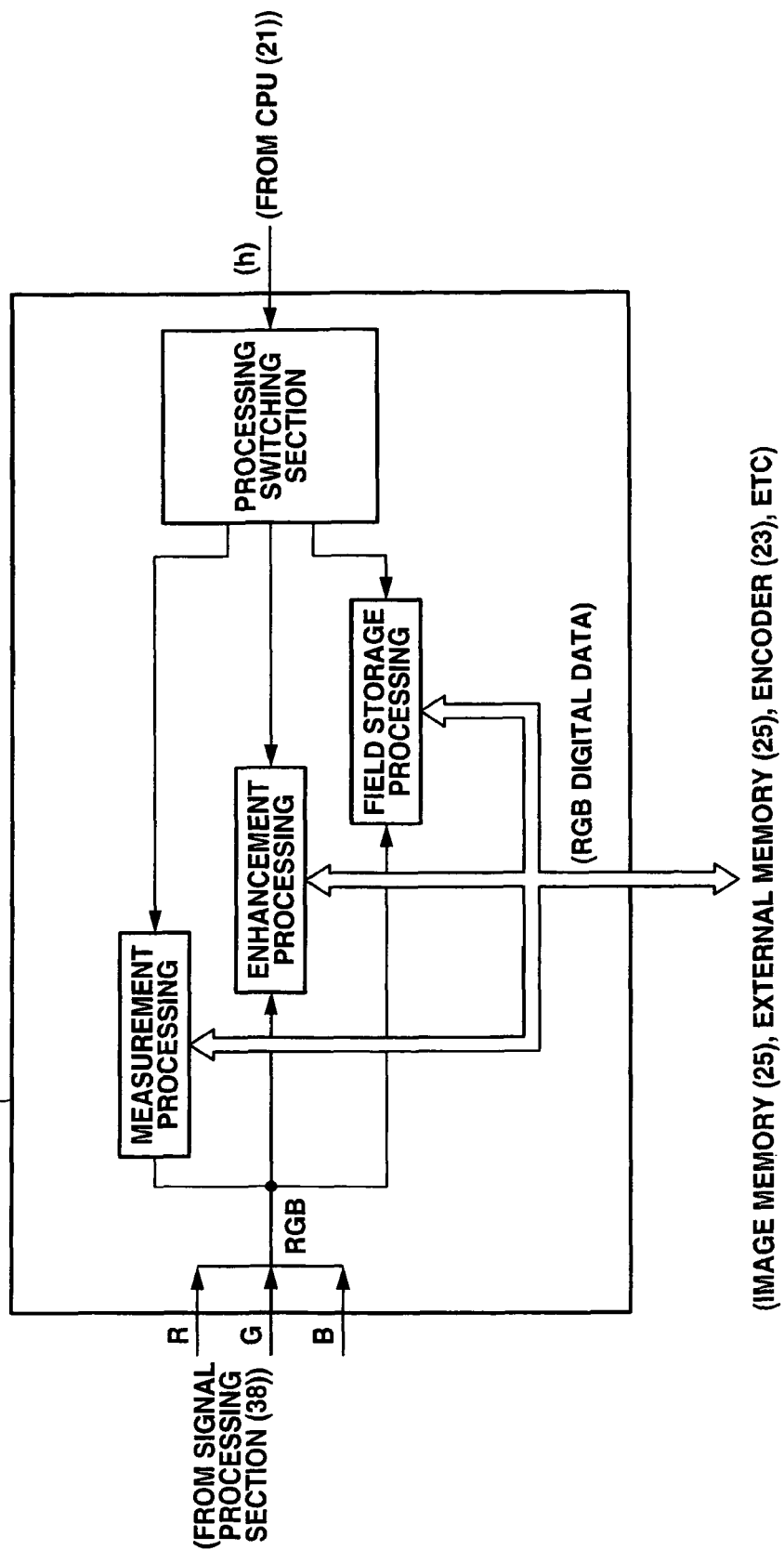
FIG. 16 is a diagram schematically showing an internal circuit configuration of an image processing section extracted from the components of the endoscope system in FIG. 1.

The setting control signal h is a control signal for setting various set values and the like for image processing control (enhancement processing, measurement processing, memory storing and addition processing, and the like) by an image processing section 22 (See FIGS. 2, 16).

Figure 17:
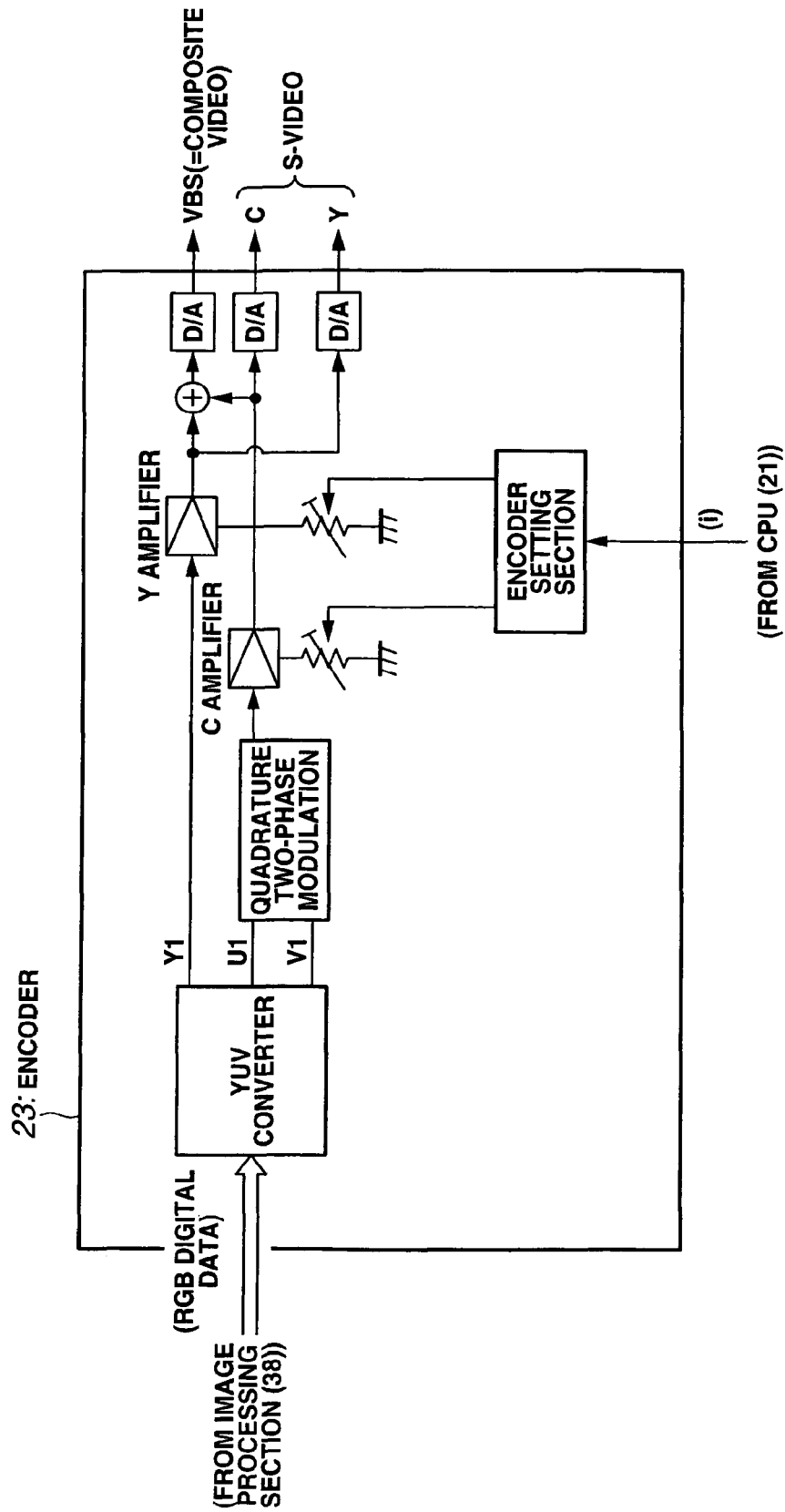
FIG. 17 is a diagram schematically showing an internal circuit configuration of an encoder extracted from the components of the endoscope system in FIG. 1.

The setting control signal i is a control signal for setting encoding level by an encoder 23 (See FIGS. 2, 17).

Figure 3:
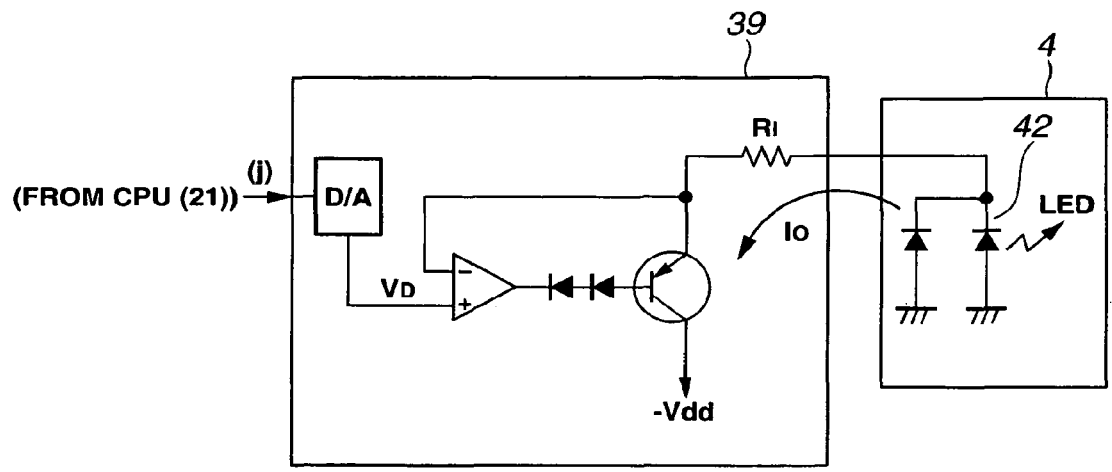
FIG. 3 is a diagram schematically showing internal circuit configurations of a part of an optical adapter (LED illumination means) and an LED drive control circuit by extracting them from the components of the endoscope system in FIG. 1.

The setting control signal j is an LED drive control signal for controlling the driving of the light-emitting diode (LED) of the optical adapter 4, and is a control signal for setting electric current amount (See FIGS. 2, 3).

Note that, other than the above-described signals, a control signal m is outputted from the adapter detection section 24 to the CPU 21, as shown in FIG. 2. The control signal m is a command control signal, from the adapter detection section 24, as a result of detecting the resistance value of the resistor 43 of the optical adapter 4 attached to the distal end of the insertion section 31.

Next, a configuration of the optical adapter 4 will be described below.

As described above, the optical adapter 4 is the LED illumination built-in type optical adapter and detachably provided to the distal end of the insertion section 31 of the endoscope section 3. That is, the optical adapter 4 includes an optical lens 45 (not shown in FIG. 1, see FIG. 2) which is image-formation optical system means for guiding light fluxes from an object of shooting onto the light-receiving surface of the image-pickup element 31*a* to form an image of the object of shooting, an aperture 44 (not shown in FIG. 1, see FIG. 2) which is aperture means for restricting the light fluxes transmitting through the optical lens 45 to be guided to the image-pickup element 31*a*, at least one or a plurality of light-emitting diodes (hereinafter referred to as LEDs) 42 as LED illumination means, a resistor (Rn; n=1, 2, 3, . . . ) 43 as adapter discrimination means for discriminating the type of the optical adapter 4, a plurality of contact portions 41 provided corresponding to a plurality of contact portions 31*b* (described later) arranged at the distal end of the insertion section 31, and other components.

Note that diagrammatic representations of the optical lens 45 and the aperture 44, which are among the components of the optical adapter 4, are omitted in FIG. 1 to avoid making the figure complicated. In addition, only one of the plurality of optical adapters 4 is shown in FIG. 2 to illustrate an internal configuration of the optical adapter 4.

As the LEDs 42 which are the LED illumination means, employed are a white light-emitting diode used for normal illumination, an infrared light-emitting diode and an ultraviolet light-emitting diode, etc., which are used for special purpose, for emitting special light such as infrared light, ultraviolet light, and the like.

The number of the LEDs 42 is different depending on the type of the optical adapter 4 having the LEDs built-in. It is configured that one optical adapter 4 has at least one or a plurality of LEDs 42 built-in.

As the aperture 44 which is aperture means, a fixed aperture is used to set a fixed aperture value (FNo.) in each optical adapter 4. That is, each of the plurality of optical adapters 4 has a specific aperture value (FNo.) respectively set according to the each aperture 44 and the each optical lens 45.

The plurality of types of optical adapters 4 are configured by combining and setting each of the aperture values (FNo.), the number of the LEDs 42, the type of the LEDs 42, and the like, according to various intended purposes.

The resistors 43 are set such that each of the resistance values thereof is specific to each of the plurality of types of optical adapters 4.

Therefore, when a predetermined optical adapter 4 is attached to the distal end of the insertion section 31, the CPU 21 in the apparatus main body 2 receives a signal from the adapter detection section 24 and detects the resistance value of the resistor 43 of the attached optical adapter 4. This enables the type of the attached optical adapter 4 to be detected (described later in detail, see FIG. 4).

For example, the plurality of types of optical adapters 4 can be configured in such a manner as shown by the numerals 4A, 4B, and 4C in FIG. 1, respectively.

Specifically, the optical adapter 4A in FIG. 1 has one LED 42 and the resistor 43 of which resistance value is R1. The optical adapter 4B has two LEDs 42 and the resistor 43 of which resistance value is R2. The optical adapter 4C has three LEDs 42 and the resistor 43 of which resistance value is R3.

Note that more specific examples of the types of the optical adapters 4 are shown in FIG. 18.

Next, description will be made on a configuration of the endoscope section 3 below.

As described above, the endoscope section 3 mainly includes the camera control unit (hereinafter abbreviated as CCU) 30, the insertion section 31, and the like.

The insertion section 31 includes an elongated flexible tube section and a bending section provided to the distal end side of the flexible tube section and formed to be freely bendable vertically and horizontally which are integrally formed. The structure of the endoscope section is similar to that of a conventional and normal endoscope, so that description on detailed configuration thereof will be omitted.

The endoscope section has, near the distal end of the insertion section 31, for example the image-pickup element 31a such as a CCD (Charge Coupled Device) which is a photoelectric conversion element, and a plurality of contact portions 31b for securing electrical connection between the insertion section 31 and the optical adapter 4 by contacting the plurality of contact portions 41 of the optical adapter 4.

The CCU 30 includes inside thereof an SSG 32 for generating a signal for driving the image-pickup element 31a, a preamplifier (PreAmp.) 33 for receiving a signal from the image-pickup element 31a, the gain control amplifier (GCA) circuit 34 for receiving an output signal from the preamplifier 33 to perform predetermined signal processing on the signal, an APL (Average of Picture Range; Average Picture Level) circuit 35 for receiving an output signal (YUV signal) from the GCA circuit 34 to perform predetermined signal processing on the signal, the gamma (γ) correction section 36 for receiving the output signal (YUV signal) from the GCA circuit 34 via an A/D converter to perform predetermined signal processing on the signal, the wide dynamic range circuit (shown as wide D range in the drawings) 37 for receiving an output signal (Y"U"V" signal) from the gamma (γ) correction section 36 to perform predetermined signal processing on the signal, the signal processing section 38 for receiving an output signal (Y"U"V" signal) from the wide dynamic range circuit 37 to perform predetermined signal processing on the signal and output RGB signals, a constant current circuit 39 which is the LED drive control circuit for making the LED 42 of the optical adapter 4 emit light, and the like.

As shown in FIGS. 2 and 3, the constant current circuit 39 as the LED drive control circuit is constituted of a standard voltage-current conversion circuit for performing constant-current control by converting the VD voltage into current. The constant current circuit 39 has a circuit configuration in which a transistor, which is connected according to constant voltage potential inputted from an operational amplifier, draws the constant current Io (See numerical expression 1).

$$Io = \frac{V_D}{R_I} \qquad (1)$$

As shown in FIG. 2, the SSG 32 receives the CCD drive control signal d, which is a setting control signal from the CPU 21, to generate a horizontal drive pulse H, vertical drive pulse V, and reset pulse R, which are signals for driving the image-pickup element 31a, and transmits these drive signals (H, V, R) to the image-pickup element 31a.

The CCD drive control signal d is a setting control signal for controlling the driving of the image-pickup element 31a, and controls the exposure operation longer than 1/60 seconds by temporarily stopping the readout operation by the image-pickup element 31a.

In addition, an electronic shutter control pulse c, which is a setting control signal for controlling the electronic shutter of the image-pickup element 31a, is transmitted from the CPU 21 to the image-pickup element 31a via the switch SW. The switch SW causes the electronic shutter function of the image-pickup element 31a to operate as a result of on/off control and second-basis time control of on-state/off-state being performed in response to the electronic shutter control pulse c from the CPU 21. Note that, when the switch SW is in the on-state (ON), the electronic shutter function is controlled to be faster than 1/60 seconds by the electronic shutter control pulse c.

The GCA circuit 34 is a circuit for receiving an image signal obtained by the image-pickup element 31a and transmitted via the PreAmp. 33, and performing automatic gain control (AGC) processing such as an amplification control or suppression control on the image signal. When the AGC processing is performed, as shown in FIGS. 2 and 5, the maximum AGC gain value and the minimum AGC gain value are set by the setting control signal a (MAX) and a (min) from the CPU 21. Then, the signal processed in the GCA circuit 34 is outputted as the YUV signal to the APL circuit 35 and (via the A/D converter) to the γ correction section 36.

As shown in FIGS. 1, 2, and 5, the APL circuit 35 receives the output signal (YUV signal) from the GCA circuit 34, and performs smoothing processing on the received signal with a LPF (low-pass filter) to convert the signal into a DC level, and then performs amplifying processing on the signal. Then, the APL circuit performs addition processing by an adder on the above signal and a setting signal of brightness reference set value (Brightness) set by the BT in response to the setting control signal b from the CPU 21. Feedback processing is performed by outputting the adding-processed signal to a variable gain (Gain) controller of the GCA circuit 34. In response to this, the GCA circuit 34 performs processing of setting a set value of the variable gain controller.

That is, the GCA circuit 34 and the APL circuit 35, in cooperation with each other, performs the level correction processing corresponding to the optical adapter 4 attached to the distal end of the insertion section 31 on the image signal obtained by the image-pickup element 31a and inputted to the GCA circuit 34 via the PreAmp. 33.

Figure 6:
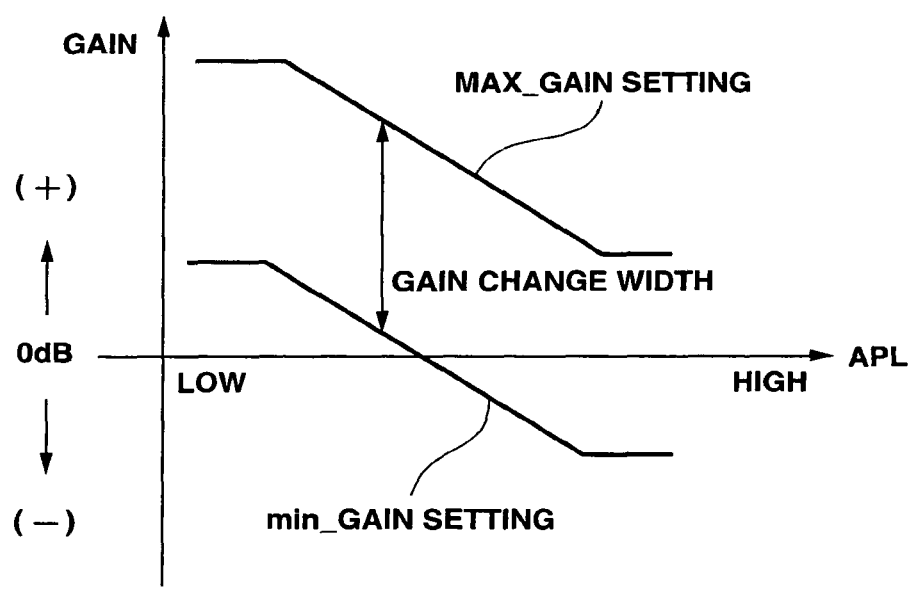
FIG. 6 is a diagram describing a gain width when performing AGC processing by the GCA circuit in FIG. 5.

Now, description will made on a gain width in the AGC processing by the GCA circuit 34 with reference to FIG. 6.

In FIG. 6, the vertical scale represents the amplification rate by the GCA circuit 34. The plus (+) direction represents the amplification direction and the minus (−) direction represents the suppression direction. Note that 0 db shows 1× magnification.

On the other hand, in FIG. 6, the horizontal scale shows the brightness level by the APL circuit 35. In this case, the lower the APL is, the lower the brightness level of the whole image is. To the contrary, the higher the APL is, the higher the brightness level of the whole image is.

The curve of MAX_Gain set value and the curve of min_Gain set value in FIG. 6 each can be set in the GCA circuit 34. The setting is performed based on the setting control signals a (MAX) and a (min) from the CPU 21. That is, the setting is performed based on the set value of the setting control data which the CPU 21 read in from the ROM 29 according to the attached optical adapter 4.

The GCA circuit 34 performs processing of changing the amplification level or suppression level within the range of the gain change width defined by the maximum gain value and the minimum gain value which are set according to the brightness condition of the image based on the image signal obtained by the image-pickup element 31a.

Therefore, in a case where the APL of the image signal is low (dark image), the GCA circuit 34 sets the maximum gain value larger, since amplification of the signal is required. On the other hand, in a case where the APL of the image signal is high (bright image), the GCA circuit 34 sets the maximum gain value smaller, since amplification of the signal is not required. The minimum gain value is set so as to have a predetermined gain change width depending on the maximum gain value set in the above-described way.

Figure 7:
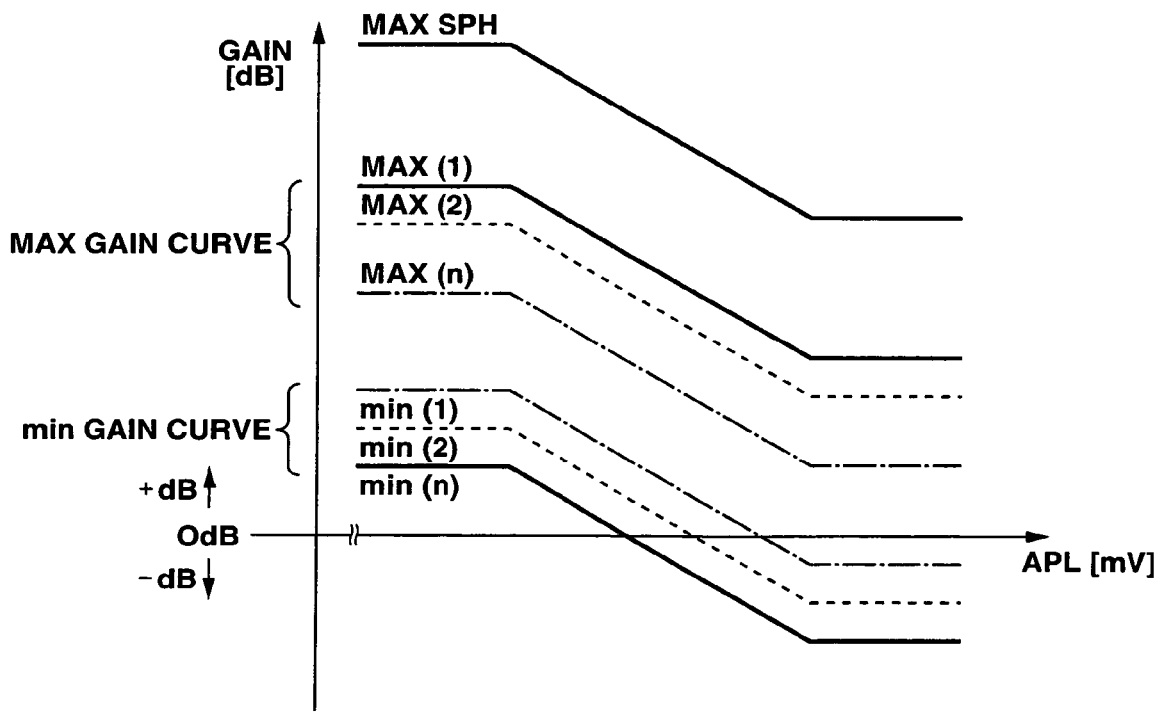
FIG. 7 is a diagram describing selection conditions of gain curves by the GCA circuit in FIG. 5.

In addition, as shown in the example of FIG. 7, the gain curve by the GCA circuit 34 is selected from a plurality of MAX gain setting curves and min gain setting curves depending on the attached optical adapter 4.

As shown in FIG. 8, the γ correction section 36 includes a lookup table (LUT) circuit 36a and a lookup data switching section 36b and the like.

In the γ correction section 36, when the signal (YUV signal) is inputted from the GCA circuit 34, the LUT 36a is referred to, and the signal conversion processing corresponding to the attached optical adapter 4 is performed on the signal. The output signal after the processing (Y'U'V' signal) is outputted to the wide dynamic range circuit 37.

The lookup table data referred to in the signal conversion processing is setting control data read into the CPU 21 from the ROM 29 on the basis of the detection result of the optical adapter 4. The setting control data is transmitted as the setting control signal e from the CPU 21 to the lookup data switching section 36b in the γ correction section 36. The lookup table switching section 36b performs γ correction processing based on the setting control signal e. The γ correction processing in this case is performed based on the input/output characteristics shown in FIG. 9.

The wide dynamic range circuit 37 is a circuit for receiving the image signal (Y'U'V' signal) from the γ correction section 36 to perform a correction so that the luminance distribution of the brightness level of the signal becomes standard, and further performing, on the correction-processed signal, wide dynamic range processing such as brightness correction processing or dark correction processing on brightness luminance distribution depending on the attached optical adapter 4, to output the image signal (Y"U"V" signal) to the image processing section 38. In this case, the wide dynamic range circuit 37 controls the wide dynamic range processing, based on the setting control signal f from the CPU 21 and the result signal (See FIGS. 11 to 13) by pre-histogram processing (See FIG. 10).

The wide dynamic range signal processing is a processing in which the whole region of an image formed based on the inputted image signal is divided into a plurality of areas (more minutely, division by pixel is possible), and gain correction processing such as brightness level correction processing of the image is performed for each signal corresponding to each divided area. Specifically, the gain correction processing performed in this case is a processing in which histogram processing is performed for each signal corresponding to each divided area to generate each luminance distribution signal, and gain correction value (k factor) for each area signal is obtained by calculation based on the luminance distribution signal.

Note that a flow of the specific operation in the wide dynamic range signal processing will be described in detail later (See FIGS. 10 to 14).

The signal processing circuit 38 receives the image signal (Y"U"V" signal) from the above-described wide dynamic range circuit 37, and performs color correction processing depending on the optical adapter 4 to convert the Y"U"V" signal into RGB signals. In this case, the color correction processing by the image processing section 38 is controlled based on the setting control signal g from the CPU 21.

Next, a configuration of the apparatus main body 2 will be described in detail.

The apparatus main body 2 includes inside thereof, for example, the CPU 21 for controlling the whole endoscope system 1, the image processing section 22 for receiving an image signal outputted from the endoscope section 3 to perform predetermined signal processing, the encoder 23 for receiving the output signal from the image processing section 22 to perform predetermined signal processing, the adapter detection section 24 for detecting the type of the optical adapter 4, an image memory 25 for temporarily storing a generated image signal, an external memory medium 26, detachably provided to the slot portion (not shown particularly) of the apparatus main body 2, for storing image data, various setting data, and the like, the ROM 29, constituted of EEPROM and the like, for example, which is storage means in which various kinds of data for generating setting control signals (reference numerals b to i in FIG. 2) from the CPU 21 are stored in advance, the DC battery 28 (See FIG. 1) as a DC power source, which is built in the apparatus main body 2, a power source section 27 (See FIG. 1) for receiving electric power supplied from power sources (an external AC power source, the DC battery 28, etc.) and controlling a supply of electric power to each circuit in the endoscope system 1.

Note that, in FIG. 2, diagrammatic representations of components constituting power sources (the DC battery 28, the power source, the power source section 27, and the like) are omitted in order to avoid making the figure complicated.

As shown in FIG. 16, the image processing section 22 performs signal processing such as image measuring processing, enhancement processing, field storage processing, and the like, on the image signals (the RGB signals) from the image processing section 38 of the endoscope section 3. The processing switching section of the image processing section 22 controls to switch which one of the signal processings is to be performed based on the setting control signal h from the CPU 21.

Note that the image measuring processing includes signal processing such as stereo processing and the like, for example. In addition, the enhancement processing includes contour emphasis processing, color emphasis processing on a specific color, and the like. Furthermore, the field storage processing is a signal processing for obtaining a sensitization effect by storing brightness signals for each field screen to perform addition processing thereon.

The encoder 23, as shown in FIG. 17, receives an image signal (RGB signal=digital data), converts the signals into the YUV signal by a YUV converter, and performs a processing of converting the YUV signal into an image signal suitable for image display on the display device 5, which is a standard television signal such as NTSC signal, PAL signal, or the like, for example. Specifically, the encoder 23 sets the gains of the luminance signal and chroma (color) signal according to setting control by an encoder setting section based on the setting control signal i from the CPU 21.

The adapter detection section 24 includes an adapter detection circuit for discriminating the type of the optical adapter 4 attached to the distal end of the insertion section 31, by detecting the adapter discrimination means (resistor (Rn) 43) of the optical adapter 4. The adapter detection section 24 is connected to the resistor 43 built in the optical adapter 4 (See FIGS. 1, 2, and 4)

The CPU 21 detects the resistance value of the resistor 43 and discriminates the type of the attached optical adapter 4 based on the detected resistance value and predetermined data stored in the ROM 29.

The predetermined data stored in advance in the ROM 29 include various setting data specific to each of the plurality of optical adapters 4, as shown in FIG. 18, for example.

That is, the CPU 21 reads from the ROM 29 the setting data corresponding to the optical adapter 4 attached to the distal end of the insertion section 31 at the time of the discrimination, based on the discrimination result of the type of the optical adapter 4 detected by the adapter detection section 24. Then, based on the setting data read from the ROM 29, the CPU 21 transmits the appropriate setting control signal (reference symbols a (MAX), a (min), b to i in FIG. 2) corresponding to the attached optical adapter 4 to each of the corresponding signal processing circuits or the like. In addition, the CPU 21 controls the constant current circuit 39 which is the LED drive control circuit by transmitting the setting control signal j based on the setting data read from the ROM 29.

The display device 5 for displaying an endoscope image, etc. is constituted of a liquid crystal display device (LCD) or the like, and is electrically connected to the encoder section 23 of the apparatus main body 2.

Below, description will be made on an operation of the endoscope system 1 thus configured according to the present embodiment.

At first, the optical adapter 4 corresponding to an intended purpose of use is attached to the distal end of the insertion section 31 of the endoscope section 3 according to a predetermined procedure. The endoscope system 1 is started up and put into a usable state by operating a power switch and the like (not shown specifically) provided to the apparatus main body 2.

After the endoscope system 1 has been started up and a predetermined initialization operation at the time of start-up has been executed, the CPU 21 receives the control signal m from the adapter detection section 24. The adapter detection section 24 discriminates the type of the optical adapter 4 attached to the distal end of the insertion section 31 of the endoscope section 3.

Figure 4:
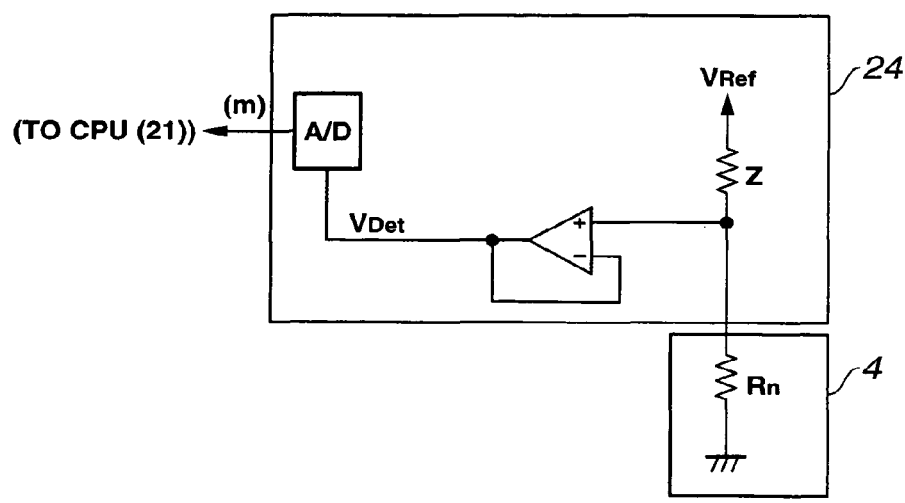
FIG. 4 is a diagram schematically showing internal circuit configurations of a part of the optical adapter (adapter discrimination means) and an adapter detection section extracted from the components of the endoscope system in FIG. 1.

That is, as shown in FIGS. 2 and 4, the adapter detection section 24 detects the voltage value divided by the resistor 43 of the optical adapter 4 and the resistor Z connected to the reference voltage (Vref) by voltage and transmits the detection signal (VDet) to the CPU 21 via the A/D converter. In response to this, the CPU 21 calculates the resistance value of the resistor 43 based on the following numerical expression 2.

$$V_{Det} = \frac{Rn}{Z + Rn} \cdot V_{Ref} \quad (2)$$

Then, the CPU 21 discriminates the type of the attached optical adapter 4 based on the calculated resistance value of the resistor 43 and the predetermined data stored in the ROM 29.

When discriminating the type of the optical adapter 4 attached to the distal end of the insertion section 31, the CPU 21 reads from the ROM 29 the setting data corresponding to the optical adapter 4 which is being attached at the time of the discrimination, based on the discrimination result.

Note that specific setting examples of the respective setting control signals (a (MAX), a (min), b to j) for typical types among a plurality of optical adapters 4, that is a part of the various types of setting data stored in advance in the ROM 29, are shown in FIG. 19.

Next, the CPU 21 transmits the LED drive control signal j, which is a setting control signal, to the constant current circuit 39 to control the driving of the light-emitting diode (LED) 42. In response to this, the constant current circuit 39 sets the most suitable current amount corresponding to the type of the optical adapter 4 detected by the adapter detection section 24. The current amount is set according to the number of LEDs 42 built in the optical adapter 4 attached to the distal end of the insertion section 31.

Specifically, the setting control signal (LED drive control signal) j is set as follows.

That is, in a case where the optical adapter 4 attached to the distal end of the insertion section 31 is, for example, a type for large-diameter endoscope, the number of light-emitting diodes 42 provided thereto is large, and the aperture value thereof is small (for example, 80 D/FF), drive current for driving fourteen white light-emitting diodes (LEDs) 42 is set (See the item (A) in the columns of the type of optical adapter in FIGS. 18 and 19).

On the other hand, in a case where the optical adapter 4 attached to the distal end of the insertion section 31 is, for example, a type for small-diameter endoscope, the number of light-emitting diodes 42 provided thereto is small, and the aperture value thereof is large (for example 120 S/NF), drive current for driving twelve white light-emitting diodes (LEDs) 42 is set, since the image tends to be dark (See the item (B) in the columns of the type of optical adapter in FIGS. 18 and 19).

In addition, in a case where the optical adapter 4 attached to the distal end of the insertion section 31 is, for example, a type for measurement (for example, 60 D/60 D), driving current for driving ten white light-emitting diodes (LEDs) 42 is set (See the item (C) in the columns of the type of optical adapter in FIGS. 18 and 19).

Furthermore, in a case where the optical adapter 4 attached to the distal end of the insertion section 31 is, for example, a type for special purpose such as infrared observation and the like (for example, 80 D), driving current for driving eight infrared light-emitting diodes (LEDs) 42 is set (See the item (D) in the columns of type of optical adapter in FIGS. 18 and 19).

Next, the CPU 21 transmits the setting control signals c, d to the SSG 32 to start driving the image-pickup element 31a. The setting control signal (electronic shutter pulse) c is specifically set as follows.

That is, in a case where the optical adapter 4 attached to the distal end of the insertion section 31 is, for example, the type for large-diameter endoscope, the number of light-emitting diodes 42 provided thereto is large, and the aperture value thereof is small (80 D/FF), the electronic shutter function is enabled and set so that the shutter speed control can be performed within a range from 1/60 to 1/10000 seconds (See the item (A) in the columns of the type of optical adapter in FIGS. 18 and 19).

On the other hand, in a case where the optical adapter 4 attached to the distal end of the insertion section 31 is, for example, the type for small-diameter endoscope, the number of light-emitting diodes 42 provided thereto is small, and the aperture value thereof is large (for example, 120 s/NF), an extremely high-speed shutter function is considered to be unnecessary, since the image is dark. Therefore, in this case, the electronic shutter function is enabled and set so that the shutter speed control can be performed within a range from 1/60 to 1/120 seconds (See the item (B) in the columns of the type of optical adapter in FIGS. 18 and 19).

In addition, in a case where the optical adapter 4 attached to the distal end of the insertion section 31 is, for example, the type for measurement (for example, 60 D/60 D), the optical adapter is often used for an observation in which an object to be measured exists close to the adapter. Therefore, it is desirable that high-speed shutter speed control can be performed to prevent a white compression phenomenon which causes deterioration in measuring precision, as much as possible. Therefore, the electronic shutter function is enabled in this case and set so that the shutter speed control can be performed within a range from 1/60 to 1/20000 seconds (See the item (C) in the columns of the type of optical adapter in FIGS. 18 and 19).

In a case where the optical adapter 4 attached to the distal end of the insertion section 31 is, for example, the type for special purpose such as infrared observation and the like (for example, 80 D), the electronic shutter function is unnecessary, so that the electronic shutter function is disabled (See the item (D) in the columns of the type of optical adapter in FIGS. 18 and 19).

In addition, the setting control signal (CCD drive control signal) d is specifically set as follows.

That is, in a case where the optical adapter 4 attached to the distal end of the insertion section 31 is, for example, the type for large-diameter endoscope, the number of light-emitting diodes 42 provided thereto is large, and the aperture value thereof is small (for example, 80 D/FF), the long-time exposure setting is enabled and it is set that the shutter speed control can be performed within a range from 2 to 1/60 seconds (See the item (A) in the columns of the type of optical adapter in FIGS. 18 and 19).

On the other hand, in a case where the optical adapter 4 attached to the distal end of the insertion section 31 is, for example, the type for small-diameter endoscope, the number of light-emitting diodes 42 provided thereto is small, and the aperture value thereof is large (for example, 120 S/NF), the image tends to be dark. Therefore, the long-time exposure setting is enabled, and it is set that the shutter speed control can be performed within a range from 4 to 1/60 seconds (See the item (B) in the columns of the type of optical adapter in FIGS. 18 and 19).

In addition, in a case where the optical adapter 4 attached to the distal end of the insertion section 31 is, for example, the type for measurement (for example, 60 D/60 D), the long-time exposure setting is disabled to prevent a deterioration in the measuring precision (See the item (C) in the columns of the type of optical adapter in FIGS. 18 and 19).

Furthermore, in a case where the optical adapter 4 attached to the distal end of the insertion section 31 is, for example, the type for special purpose such as infrared observation and the like (for example, 80 D), the long-time exposure setting is enabled and it is set that the shutter speed control can be performed within a range from 10 to 1/60 seconds (See the item (D) in the columns of the type of optical adapter in FIGS. 18 and 19).

In a case where the optical adapter 4 attached to the distal end of the insertion section 31 is, for example, the type for special purpose such as fluorescent observation and the like, and is an ultraviolet LED (for example, 80 D), the gain of the AGC is set intermediately as MAX(2), and min (2). In addition, the electronic shutter is enabled.

Also, the long-time exposure setting is enabled. In fluorescent observations, it is often the case that a spot-like luminescent point is found out and inspected by using an ultraviolet illumination. Therefore, for the purpose of performing positive brightness correction, brightness correction is performed on the γ as well as the wide D range. Furthermore, to make the color tone difference of defective spots clear, only the c (color) level is doubled by the encoder. Since the color level is doubled, the color SN ratio tends to deteriorate. Therefore, in order to correct the tendency, field storage sensitization is enabled to improve the SN ratio (See the item (E) in the columns of the type of optical adapter in FIGS. 18 and 19).

When the driving of the image-pickup element 31a is started as described above, an image signal is obtained. Then, after predetermined amplification processing is performed in the PreAmp. 33 on the obtained image signal, the image signal is inputted to the GCA circuit 34 via the PreAmp 33.

In response to this, the GCA circuit 34 executes AGC processing in cooperation with the APL circuit 35 to generate the image signal (YUV signal). The CPU 21 transmits the setting control signal a (MAX) for setting the maximum gain value and the setting control signal a (min) for setting the minimum gain value to the GCA circuit 34. At the same time, the CPU 21 transmits the setting control signal b to the APL circuit 35. The setting control signals (AGC maximum gain value a (MAX) and AGC minimum gain value a (min)) are specifically set as follows in each case.

That is, in a case where the optical adapter 4 attached to the distal end of the insertion section 31 is, for example, the type for large-diameter endoscope, the number of light-emitting diodes 42 provided thereto is large, the aperture value thereof is small (for example 80 D/FF), an image to be obtained is brighter. Therefore, in this case, the MAX_(n) among a plurality of MAX_Gain setting curves and min (n) among a plurality of min_Gain setting curves shown in FIG. 7 are selected (See the item (A) in the columns of the type of optical adapter in FIGS. 18 and 19).

On the other hand, in a case where the optical adapter 4 attached to the distal end of the insertion section 31 is, for example, the type for small-diameter endoscope, the number of light-emitting diodes 42 provided thereto is small, and the aperture value thereof is large (for example 120 S/NF), an image to be obtained is darker. Therefore, in this case, the MAX_(1) among a plurality of MAX_Gain setting curves and min (1) among a plurality of min_Gain setting curves shown in FIG. 7 are selected (See the item (B) in the columns of the type of optical adapter in FIGS. 18 and 19).

In addition, in a case where the optical adapter 4 attached to the distal end of the insertion section 31 is, for example, the type for measurement (for example, 60 D/60 D), the MAX_(1) among a plurality of MAX_Gain setting curves and min (n) among a plurality of min_Gain setting curves shown in FIG. 7 are selected. That is, in this case, the gain change width is set to be larger (See the item (C) in the columns of the type of optical adapter in FIGS. 18 and 19).

In a case where the optical adapter 4 attached to the distal end of the insertion section 31 is, for example, the type for special purpose such as infrared observation and the like (for example, 80 D), the MAX (SPH) among a plurality of MAX_Gain setting curves and min (1) among a plurality of min_Gain setting curves shown in FIG. 7 are selected. That is, in this case, the maximum gain value is set by giving priority thereto (See the item (D) in the columns of the type of optical adapter in FIGS. 18 and 19).

In a case of fluorescent observation, and the optical adapter is ultraviolet light illumination, the intermediate MAX (2) and min (2) are selected among the MAX and min gain curves, respectively, so as not to extremely increase the MAX gain and not to extremely decrease the min gain (See the item (E) in the columns of the type of optical adapter in FIGS. 18 and 19).

In addition, the setting control signal b is specifically set as follows in each case. That is, in a case where the optical adapter 4 attached to the distal end of the insertion section 31 is, for example, the type for observation (for example, 80 D/FF or 120 S/NF), standard setting (S) is performed, thereby facilitating visual observation (See the items (A) (B) in the columns of the type of optical adapter in FIGS. 18 and 19).

In a case where the optical adapter 4 attached to the distal end of the insertion section 31 is, for example, the type for measurement (for example 60 D/60 D), a setting (S-L) which is a little darker than the standard setting (S) is performed. Image measuring processing is normally performed in proximal observation. In an image obtained by a proximal observation, a white compression tendency is seen, because of proximity to an illumination light source. That is why, in a case of the optical adapter for measurement, a little darker setting is performed to prevent white compression from occurring in the image (See the item (C) in the columns of the type of optical adapter in FIGS. 18 and 19).

In a case where the optical adapter 4 attached to the distal end of the insertion section 31 is, for example, the type for special purpose (infrared observation and the like) (for example, 80 D), a setting (S-H) which is a little brighter than the standard setting (S) is performed to give priority to brightness (See the item (D) in the columns of the type of optical adapter in FIGS. 18 and 19).

The image signal (YUV signal) thus generated is outputted from the GCA circuit 34 to the γ correction section 36 via the A/D converter.

The γ correction section 36 receives the image signal and performs predetermined γ correction processing on the received image signal to generate the image signal (Y'U'V' signal). For this, the CPU 21 transmits a setting control signal e to the γ correction section 36. The setting control signal e is specifically set as follows in each case.

Figure 9:
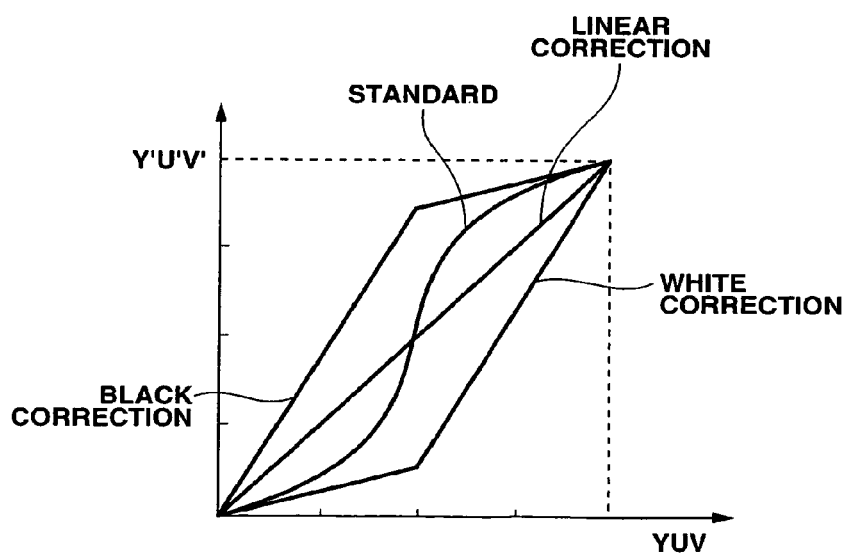
FIG. 9 is a diagram describing input-output characteristics of γ correction processing in the gamma (γ) correction section in FIG. 8.

That is, in a case where the optical adapter 4 attached to the distal end of the insertion section 31 is, for example, the type for large-diameter endoscope, the number of light-emitting diodes 42 provided thereto is large, and the aperture value thereof is small (for example, 80 D/FF), the standard curve shown in FIG. 9 is selected (See the item (A) in the columns of the type of optical adapter in FIGS. 18 and 19).

On the other hand, in a case where the optical adapter 4 attached to the distal end of the insertion section 31 is, for example, the type for small-diameter endoscope, the number of light-emitting diodes 42 provided thereto is small, and the aperture value thereof is large (for example, 120 S/NF), the black correction curve shown in FIG. 9 is selected in order to perform processing for giving priority to brightness (See the item (B) in the columns of the type of optical adapter in FIGS. 18 and 19).

In addition, in a case where the optical adapter 4 attached to the distal end of the insertion section 31 is, for example, the type for measurement (for example, 60 D/60 D), the linear correction curve shown in FIG. 9 is selected in order to secure accuracy of the image measuring processing and to prevent a deterioration in measuring precision (See the item (C) in the columns of the type of optical adapter in FIGS. 18 and 19).

Furthermore, in a case where the optical adapter 4 attached to the distal end of the insertion section 31 is, for example, the type for special purpose such as infrared observation and the like (for example, 80 D), the black correction curve shown in FIG. 9 is selected. Or, though not shown, a curve for special correction which is specially and exclusively considered may be used (See the item (D) in the columns of the type of optical adapter in FIGS. 18 and 19).

Note that, though not exemplified, the white correction curve shown in FIG. 9 is applied to a case where the whole image is bright and white compression occurs in the image, for example.

The image signal (Y'U'V' signal) thus generated is outputted from the γ correction section 36 to the wide dynamic range circuit 37.

The wide dynamic range circuit 37 receives the image signal and executes predetermined wide dynamic range processing on the received image signal to generate the image signal (Y"U"V" signal). Now, details of the wide dynamic range processing will be described below.

Figure 12:
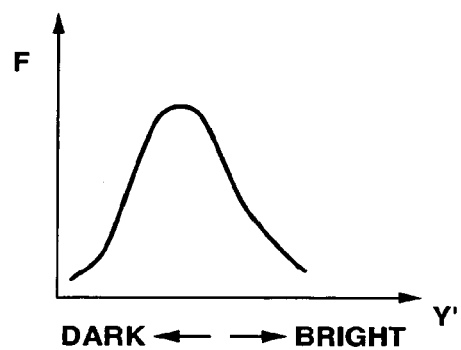
FIG. 12 is an exemplification of a result signal of pre-histogram processing performed in the wide dynamic range circuit in FIG. 10 and is a diagram showing a luminance distribution signal of an image of standard brightness.
Figure 13:
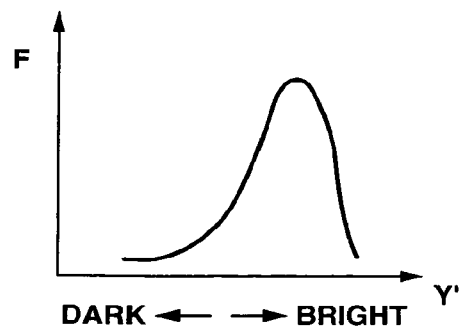
FIG. 13 is an exemplification of a result signal of pre-histogram processing performed in the wide dynamic range circuit in FIG. 10 and is a diagram showing a luminance distribution signal of a bright image.

At first, the wide dynamic range circuit 37 receives the Y'U'V' signal from the γ correction section 36 and performs pre-histogram processing on the received signal, as shown in FIG. 10. As a result, luminance distribution signals as shown in FIGS. 11 to 13 are outputted.

Figure 11:
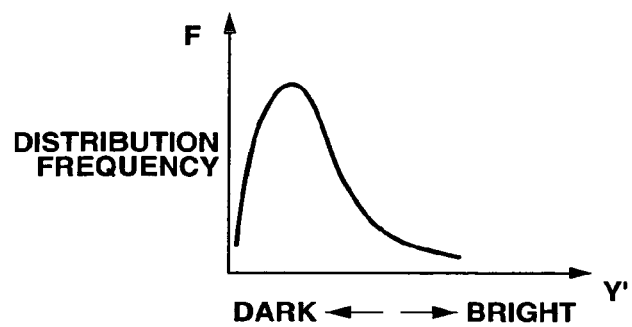
FIG. 11 is an exemplification of a result signal of pre-histogram processing performed in the wide dynamic range circuit in FIG. 10 and is a diagram showing a luminance distribution signal of a dark image.

For example, the luminance distribution signal shown in FIG. 11 is an example of a case where the image is dark and black compression (a state where gradation is lost in a shadow portion of an image) occurs in the image. The luminance distribution signal shown in FIG. 12 is an example of an image with standard brightness. The luminance distribution signal shown in FIG. 13 is an example of a case where the image is bright and white compression (a state where gradation is lost in a highlight portion of an image) occurs in the image.

The luminance distribution signal outputted as a result of the above-described pre-histogram processing (See FIGS. 11 through 13) is transmitted to the CPU 21 via a histogram processing monitoring section and a brightness level of an image formed based on the Y'U'V' signal from the γ correction section 36 is discriminated.

As a result of the discrimination, the CPU 21 transmits the setting control signal f to a k-factor generating section. When receiving the setting control signal, the k-factor generating section sets and outputs control factors k1, k2, k3, . . . and kl to be used for the gain correction processing performed in control amplifiers C1, C2, C3, . . . , and Cl described later.

On the other hand, at the same time, the wide dynamic range circuit 37 receives the Y'U'V' signal from the γ correction circuit 36, and performs predetermined area division processing. Then the signal corresponding to each of the plurality of divided areas is inputted to the corresponding control amplifier C1, C2, C3, . . . , and Cl, respectively. When receiving the signal, the respective control amplifiers C1, C2, C3, . . . and Cl perform predetermined gain correction processing. These plurality of control amplifiers C1, C2, C3, . . . , and Cl are controlled based on the control factors k1, k2, k3, . . . , and kl outputted from the k-factor generating section.

The respective signals corresponding to the respective areas, on which the gain correction processing is performed respectively by the control amplifiers C1, C2, C3, . . . , and Cl, are composed by the adder to be outputted as the Y"U"V" signal to the signal processing section 38.

At the same time, the generated Y"U"V" signal is outputted to the histogram processing monitoring section and the histogram processing is performed thereon.

The luminance distribution signal as a result of the histogram processing is outputted to the CPU 21. When receiving the luminance distribution signal, the CPU 21 confirms whether or not the luminance distribution signal is corrected to reach an appropriate brightness level by the above-described gain correction processing (feedback processing).

In a case where it is confirmed that the luminance distribution signal of the Y"U"V" signal has not reached an appropriate targeted brightness level, the CPU 21 transmits the predetermined control signal f generated based on the luminance distribution signal to the k-factor generating section.

The k-factor generating section resets the control factors k1, k2, k3, ... and kl and outputs the reset factors to the control amplifiers C1, C2, C3, ..., Cl.

When receiving the factors, the control amplifiers C1, C2, C3, ..., Cl perform the gain correction again on each of the plurality of divided area signals based on the Y'U'V' signal, by using the reset control factors k1, k2, k3, ... and kl.

Similar signal processing is repeated until the luminance distribution signal of the Y"U"V" signal reaches the appropriate targeted brightness level.

That is, when confirming that the luminance distribution signal of the Y"U"V" signal has reached the appropriate targeted brightness level, the CPU 21 transmits the control signal g to the signal processing section 38. In response to this, the signal processing section 38 starts predetermined signal processing on the Y"U"V" signal inputted thereto.

Note that, as shown in FIG. 10, the wide dynamic range circuit 37 has a bypass path through which the Y'U'V' signal from the γ correction section 36 can be outputted as it is to the signal processing section 38 without the above-described each processing. A switch is provided on the bypass path. The switch allows the bypass path to be in a conductive state as a result of receiving the control factor "no correction" which is outputted from the k-factor generating section in response to the control signal f from the CPU 21. The control factor "no correction" is outputted from the k-factor generating section in a case where the optical adapter 4 for measurement is attached to the distal end of the insertion section 31, for example.

The setting control signal f transmitted from the CPU 21 to the k-factor generating section in the wide dynamic range circuit 37 is specifically set as follows in each case.

That is, in a case where the optical adapter 4 attached to the distal end of the insertion section 31 is, for example, the type for large-diameter endoscope, the number of light-emitting diodes 42 provided thereto is large, and the aperture value thereof is small (for example, 80 D/FF), a setting for standard correction is performed (See the item (A) in the columns of the type of optical adapter in FIGS. 18 and 19).

On the other hand, in a case where the optical adapter 4 attached to the distal end of the insertion section 31 is, for example, the type for small-diameter endoscope, the number of light-emitting diodes 42 provided thereto is small, and the aperture value thereof is large (for example, 120 S/NF), the image tends to be dark. Therefore, a setting for brightness correction (a setting for correcting the brightness distribution of the image to brighter side) is performed (See the item (B) in the columns of the type of optical adapter in FIGS. 18 and 19).

In addition, in a case where the optical adapter 4 attached to the distal end of the insertion section 31 is, for example, the type for measurement (for example, 60 D/60 D), a setting for no correction is performed (See the item (C) in the columns of the type of optical adapter in FIGS. 18 and 19).

Furthermore, in a case where the optical adapter 4 attached to the distal end of the insertion section 31 is, for example, the type for special purpose such as infrared observation and the like (for example, 80 D), a setting for brightness correction is performed (See the item (D) in the columns of the type of optical adapter in FIGS. 18 and 19).

In a case of fluorescent observation, brightness correction is performed so as to make spot-like luminance more distinctive (See the item (E) in the columns of the type of optical adapter in FIGS. 18 and 19).

Note that, though not exemplified, the dark correction shown in FIG. 14 is applied to a case where the whole image is bright and white compression occurs in the image.

The image signal (Y"U"V" signal) thus generated is outputted from the wide dynamic range circuit 37 to the signal processing section 38.

The signal processing section 38 receives the Y"U"V" signal from the wide dynamic range circuit 37 and performs signal conversion processing on the received signal in a matrix circuit to generate RGB signals. The respective RGB signals are outputted as an RGB signal via amplifiers (R, G, B amplifiers) corresponding to the respective RGB signals. For example, the R amplifier is controlled by GR control signal from a mode switching circuit. The G amplifier is controlled by GG control signal from the mode switching circuit. The B amplifier is controlled by GB control signal from the mode switching circuit.

In this case, the color tone control signal g is transmitted from the CPU 21 to the signal processing section 38. In response to this, the mode switching circuit controls each amplifier. According to this, predetermined color correction processing is performed on the signals of respective colors.

The setting control signal g is specifically set as follows in each case. That is, in a case where the optical adapter 4 attached to the distal end of the insertion section 31 is the type for normal observation (for example, 80 D/FF or 120 S/NF) or for measurement (for example, 60 D/60 D), standard setting is performed (See the items (A), (B), (C), and (E) in the columns of the type of optical adapter in FIGS. 18 and 19).

In addition, in a case where the optical adapter 4 attached to the distal end of the insertion section 31 is, for example, the type for special purpose such as infrared observation and the like (for example, 80 D), monochrome setting for performing color correction processing to equalize R, G, and B by reducing the chromatic level is performed. Thus, in this case, a monochrome image is generated (See the item (D) in the columns of the type of optical adapter in FIGS. 18 and 19).

The image signal (RGB signal) thus generated is outputted from the signal processing section 38 to the image processing section 22 in the apparatus main body 2.

The image processing section 22 receives the RGB signal from the signal processing section 38, and sets by the processing switching section which one of the image measuring processing, enhancement processing, and field storage processing, is to be performed (enabled) or not to be performed (disabled) on each image to be processed. The processing switching section controls switching among each of the processing based on the setting control signal (image processing control signal) h from the CPU 21. The setting control signal h is specifically set as follows in each case.

That is, in a case where the optical adapter 4 attached to the distal end of the insertion section 31 is, for example, the type for large-diameter endoscope, the number of light-emitting diodes 42 provided thereto is large, and the aperture value thereof is small (for example, 80 D/FF), only the enhancement processing is set to be enabled (See the item (A) in the columns of the type of optical adapter in FIGS. 18 and 19).

In a case where the optical adapter 4 attached to the distal end of the insertion section 31 is, for example, the type for small-diameter endoscope, the number of light-emitting diodes 42 provided thereto is small, and the aperture value thereof is large (for example, 120 S/NF), the field storage sensitization processing is enabled. In this case, the sensitization processing up to four times, that is, addition processing for up to four fields, is set to be performed (See the item (B) in the columns of the type of optical adapter in FIGS. 18 and 19).

In addition, in a case where the optical adapter 4 attached to the distal end of the insertion section 31 is, for example, the type for measurement (for example, 60 D/60 D), only the measurement processing is set to be enabled (See the item (C) in the columns of the type of optical adapter in FIGS. 18 and 19).

Furthermore, in a case where the optical adapter 4 attached to the distal end of the insertion section 31 is, for example, the type for special purposes such as infrared observation, fluorescent observation, and the like (for example, 80 D), the field storage sensitization processing is enabled. In this case, sensitization processing up to sixteen times, that is addition processing for up to sixteen fields, is set to be performed (See the items (D)(E) in the columns of the type of optical adapter in FIGS. 18 and 19).

The image signal (RGB signal) thus generated is outputted from the image processing section 22 to the encoder 23.

The encoder 23 receives the image signal (RGB signal=digital data) from the image processing section 22 to generate an image signal suitable for displaying the image on the display device 5.

That is, the encoder 23 converts the inputted RGB signal (digital data) into Y1U1V1 signals (digital data) by the YUV converter. The encoder performs quadrature two-phase modulation processing on the U1 signal and the V1 signal which are related to color components to generate a chroma signal (color signal). The chroma signal passes through the chroma (c) amplifier to be outputted, after being converted from digital signal to analog signal by the D/A converter, as the chroma signal C of S-video signal (analog signal).

On the other hand, the luminance signal Y1 among the Y1U1V1 signals (digital data) converted by the YUV converter passes through the luminance (Y) amplifier to be outputted, after being converted from digital signal to analog signal by the D/A converter, as the luminance signal Y of the S-Video signal (analog signal).

In addition, aside from the above, the luminance signal Y1 (digital data) having passed through the luminance (Y) amplifier and the chroma signal (digital data) having passed through the chroma (C) amplifier are outputted, after being composed by the adder and converted from digital signal to analog signal by the D/A converter, as VBS (Composite Video) signal which is analog signal.

Note that, the levels of the chroma (C) and luminance (Y) amplifiers are controlled to be set by the encoder setting section based on the setting control signal i from the CPU 21. The setting control signal i is specifically set as follows in each case.

That is, in a case where the optical adapter 4 attached to the distal end of the insertion section 31 is the type for normal observation (for example, 80 D/FF and 120 S/NF and the like) or for measurement (for example, 60 D/60 D), standard setting is performed (See the items (A), (B), and (C) in the columns of the type of optical adapter in FIGS. 18 and 19).

In a case where the optical adapter 4 attached to the distal end of the insertion section 31 is the type for special purpose such as infrared observation and the like (for example, 80 D), the Y level and the C level are set to be 1 times and 0.1 times (one-tenth) the original levels, respectively (See the item (D) in the columns of the type of optical adapter in FIGS. 18 and 19).

In a case of fluorescent observation, only the C level is set to be doubled so as to make the color tone difference of defective spots clear (See the item (E) in the columns of the type of optical adapter in FIGS. 18 and 19).

The image signal thus generated by the encoder 23 is transmitted to the display device 5 via an S-Video terminal or a Video-out terminal, and displayed as an image.

As described above, according to the embodiment, the specific adapter discrimination means (resistors 43 each of which has a specific resistance value) is provided to each of the plurality of optical adapters 4, while the adapter detection section 24 connected to the adapter discrimination means to detect the same is provided on the side of the apparatus main body 2.

According to the configuration, when the optical adapter 4 is attached to the distal end of the insertion section 31 in using the endoscope system 1, the adapter detection section 24 operates to detect the resistor 43 which is the adapter discrimination means of the attached optical adapter 4 under the control of the CPU 21. As a result, the type of the optical adapter 4 can be automatically detected based on the resistance value of the resistor and the predetermined setting data stored in the ROM 29.

Then, at the same time, various kinds of setting data corresponding to the type of the attached optical adapter 4 are read in from the ROM 29, and based on the setting data, the driving control of the LED illumination means (LED 42) and various signal processing control on the image signal obtained by the image-pickup element 31*a* are performed. Therefore, appropriate image signal processing is always performed and excellent images meeting purposes such as observation, measurement, and the like, can be surely generated and displayed.

Though the setting data, etc., corresponding to the type of the optical adapter 4 is stored in the ROM 29 in the present embodiment, the configuration is not limited to the same.

For example, the setting data, etc., may be stored in the external memory medium 26. Then, by attaching the external memory medium to a slot portion (not shown) of the apparatus main body 2, the setting data, etc., stored in the external memory medium 26 may be read by the CPU 21, and then transferred to the ROM 29.

In addition, the setting data, etc., corresponding to the type of the optical adapter 4 may be transferred from an external computer (PC) and the like to the ROM 29 via a serial port 21*a* of the CPU 21.

In the present invention, it is apparent that different embodiments in a wide range can be adapted based on the present invention without departing from the spirit and the scope of the present invention. The present invention is not limited by particular embodiments except for being limited by the range of the attached claims.

What is claimed is:

1. An endoscope system comprising:
   an image-pickup element configured to pick up an image of an object and to output an image signal based on the picked up image;
   a main unit configured to be selectively connected to at least one of a first module and a second module,
      wherein the first module comprises:
         one or more light sources, wherein the one or more light sources are driven by the main unit;
         a first identification circuit having a first characteristic that identifies at least the quantity of the one or more light sources of the first module as a first number; and
         a first optical unit configured to form a first image of the object, and
      wherein the second module comprises:
         one or more light sources, wherein the one or more light sources are driven by the main unit;
         a second identification circuit having a second characteristic that identifies at least the quantity of the one or more light sources of the second module as a second number, wherein the second number is different from the first number; and a second optical unit configured to form a second image of the object, the main unit comprising:
  a detection circuit configured to detect the first characteristic that identifies at least the first number from the first identification circuit, upon connection of the first module to the main unit, and to detect the second characteristic that identifies at least the second number from the second identification circuit, upon connection of the second module to the main unit; and
  a control circuit configured:
    upon connection of the first module to the main unit, to control the detection circuit to detect the first characteristic that identifies at least the first number,
    after detecting the first characteristic, to perform a first condition setting, based on the first characteristic, for the image-pickup element to perform image-pickup of the first image formed by the first optical unit of the first module,
    upon disconnection of the first module from the main unit and subsequent connection of the second module to the main unit, to control the detection circuit to detect the second characteristic that identifies at least the second number, and
    after detecting the second characteristic, to perform a second condition setting, based on the second characteristic, for the image-pickup element to perform image-pickup of the second image formed by the second optical unit of the second module.

2. The endoscope system according to claim 1, wherein the control circuit is configured to perform electronic shutter control as at least one of the first condition setting and the second condition setting.

3. The endoscope system according to claim 1, wherein the control circuit is configured to perform exposure control as at least one of the first condition setting and the second condition setting.

4. The endoscope system according to claim 1, wherein the control circuit is configured to perform brightness setting control as at least one of the first condition setting and the second condition setting.

5. The endoscope system according to claim 1,
  wherein the first module and the second module are configured to be detachably and selectively connected to a distal end of an insertion section of an endoscope, and
  wherein the image-pickup element is arranged in the insertion section of the endoscope.

6. The endoscope system according to claim 1,
  wherein the main unit further comprises a storage configured to store at least a first setting control data and a second setting control data, and
  wherein the control circuit is configured:
    to read the first setting control data from the storage based on the detecting of the first characteristic, and to perform the first condition setting using the first setting control data, and
    to read the second setting control data from the storage based on the detecting of the second characteristic, and to perform the second condition setting using the second setting control data.

7. The endoscope system according to claim 1, wherein the main unit further comprises a signal processing circuit configured to perform image signal processing on the image signal output by the image-pickup element.

8. An endoscope system comprising:
  an image-pickup element configured to pick up an image of an object and to output an image signal based on the picked up image;
  a main unit configured to be selectively connected to at least one of a first module and a second module,
    wherein the first module comprises:
      one or more light sources, wherein the one or more light sources are driven by the main unit;
      a first identification section having a first characteristic that identifies at least the quantity of the one or more light sources of the first module as a first number; and
      a first optical unit configured to form a first image of the object, and
    wherein the second module comprises:
      one or more light sources, wherein the one or more light sources are driven by the main unit;
      a second identification section having a second characteristic that identifies at least the quantity of the one or more light sources of the second module as a second number, wherein the second number is different from the first number; and
      a second optical unit configured to form a second image of the object, the main unit comprising:
  a detection device configured to detect the first characteristic that identifies at least the first number from the first identification section, upon connection of the first module to the main unit, and to detect the second characteristic that identifies at least the second number from the second identification section, upon connection of the second module to the main unit; and
  control means for:
    upon connection of the first module to the main unit, to control the detection device to detect the first characteristic that identifies at least the first number,
    after detecting the first characteristic, to perform a first condition setting, based on the first characteristic, for the image-pickup element to perform image-pickup of the first image formed by the first optical unit of the first module,
    upon disconnection of the first module from the main unit and subsequent connection of the second module to the main unit, to control the detection device to detect the second characteristic that identifies at least the second number, and
    after detecting the second characteristic, to perform a second condition setting, based on the second characteristic, for the image-pickup element to perform image-pickup of the second image formed by the second optical unit of the second module.

9. The endoscope system according to claim 8, wherein the main unit further comprises a signal processing device configured to perform image signal processing on the image signal output by the image-pickup element.

10. A method for operating an endoscope system comprising:
  an image-pickup element configured to pick up an image of an object and to output an image signal based on the picked up image; and
  a main unit configured to be selectively connected to at least one of a first module and a second module,
    wherein the first module comprises:
      one or more light sources, wherein the one or more light sources are driven by the main unit;

a first identification circuit having a first characteristic that identifies at least the quantity of the one or more light sources of the first module as a first number; and a first optical unit configured to form a first image of the object, and wherein the second module comprises:

one or more light sources, wherein the one or more light sources are driven by the main unit;

a second identification circuit having a second characteristic that identifies at least the quantity of the one or more light sources of the second module as a second number, wherein the second number is different from the first number; and a second optical unit configured to form a second image of the object, the method comprising:

upon connection of the first module to the main unit, detecting the first characteristic that identifies at least the first number from the first identification circuit, after detecting the first characteristic, performing a first condition setting, based on the first characteristic, for the image-pickup element to perform image-pickup of the first image formed by the first optical unit of the first module, upon disconnection of the first module from the main unit and subsequent connection of the second module to the main unit, detecting the second characteristic that identifies at least the second number from the second identification circuit, and after detecting the second characteristic, performing a second condition setting, based on the second characteristic, for the image-pickup element to perform image-pickup of the second image formed by the second optical unit of the second module.

11. The method according to claim 10, further comprising performing image signal processing on the image signal output by the image-pickup element.

* * * * *